(12) United States Patent
Stone et al.

(10) Patent No.: US 8,401,632 B1
(45) Date of Patent: Mar. 19, 2013

(54) SYSTEMS AND METHODS FOR PERFORMING NEUROPHYSIOLOGIC ASSESSMENTS

(75) Inventors: Robert Stone, Poway, CA (US); Allen Farquhar, Portland, OR (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 12/626,880

(22) Filed: Nov. 27, 2009

Related U.S. Application Data

(60) Provisional application No. 61/118,327, filed on Nov. 26, 2008.

(51) Int. Cl.
*A61B 5/00* (2006.01)
(52) U.S. Cl. .................................................. 600/546
(58) Field of Classification Search .............. 600/546, 600/554; 702/64, 190, 191
See application file for complete search history.

(56) References Cited

U.S. PATENT DOCUMENTS

| | | | | |
|---|---|---|---|---|
| 4,344,441 A | * | 8/1982 | Radke | 600/546 |
| 5,885,231 A | * | 3/1999 | Cramer et al. | 600/595 |
| 6,001,065 A | * | 12/1999 | DeVito | 600/544 |
| 6,280,394 B1 | * | 8/2001 | Maloney et al. | 600/546 |
| 7,228,169 B2 | * | 6/2007 | Viertio-Oja et al. | 600/544 |
| 7,689,275 B2 | * | 3/2010 | Blomberg et al. | 600/546 |
| 2008/0015821 A1 | * | 1/2008 | Roushall | 702/191 |
| 2008/0069364 A1 | * | 3/2008 | Itou et al. | 381/17 |

* cited by examiner

*Primary Examiner* — Max Hindenburg
(74) *Attorney, Agent, or Firm* — Jonathan Spangler; Rory Schermerhorn; Heather Prado

(57) ABSTRACT

The present invention involves a system and methods for performing neurophysiologic assessments including, but not necessarily limited to, pedicle integrity assessments, neuromuscular pathway assessments, nerve proximity assessments, and spinal cord assessments, and methods for filtering EMG signal data to reject noise.

8 Claims, 31 Drawing Sheets

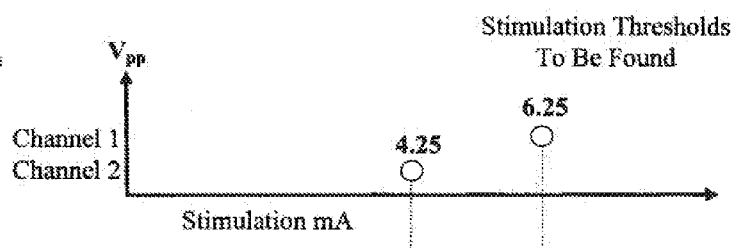
FIG. 39A
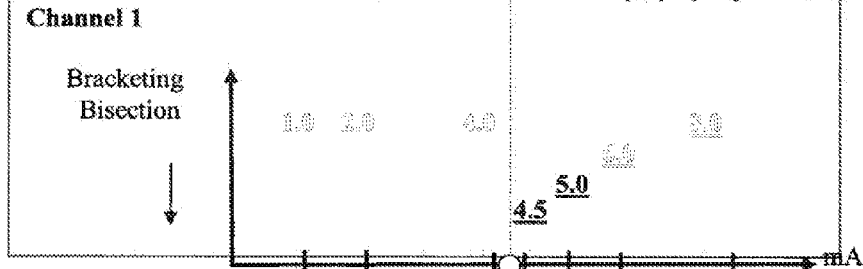
FIG. 39B
FIG. 39C

SYSTEMS AND METHODS FOR PERFORMING NEUROPHYSIOLOGIC ASSESSMENTS

CROSS-REFERENCE TO RELATED APPLICATIONS

The present application is a nonprovisional patent application and claims priority under 35 U.S.C. §119(e) from the commonly owned U.S. Provisional Patent Application Ser. No. 61/118,327, filed Nov. 26, 2008, the complete disclosure of which is incorporated by reference herein in its entirety for all purposes.

FIELD

This application relates generally to performing and monitoring neurophysiologic assessments of the spinal cord and nerve roots before, during, and after surgery, such as for example, MEP, SSEP, neuromuscular pathway, pedicle integrity, nerve proximity, and nerve pathology assessments.

BACKGROUND

It has been estimated that somewhere between 50 and 70 million people suffer from chronic back pain in the United States. In most cases, conservative therapies, including, for example, bed rest and physical therapy will succeed in alleviating, or at least significantly reducing the back pain. Still, a significant number of patients are unaided by conservative therapies alone and undergo spinal surgery before finding relief. The rate at which caregivers and patients opt for surgery also continues to grow as medical technology advances and surgical options increase. In all, approximately 750,000 spine surgeries are performed per year in the United States alone.

When necessary, spine surgery may provide great benefit to the patient, often allowing patients to resume activities long since abandoned because of the debilitating pain. Spine surgery, however, is not without risk. Operating on or near the spine generally means operating in close proximity to delicate neural tissue, such as the spinal cord and nerve roots. Damage to the neural tissue, which may be caused, for example, by inadvertent contact with a surgical instrument and/or implant or by excessive nerve retraction, may have consequences ranging from a slight loss of sensation to complete paralysis. One way to mitigate this risk is to conduct neurophysiologic monitoring during the procedure and/or recovery period. Neurophysiologic monitoring generally consists of stimulating neural tissue and analyzing responses (generally electrical waveforms) generated by the stimulus. Processing of the electrical waveform data is generally complex. The presence of electrical energy caused by sources other than the patients neuromuscular system can taint the analysis and produce unwanted results. It is thus beneficial to be able to detect such noise and ignore or filter it out of the neurophysiologic data.

SUMMARY

The present invention includes a system and related methods for performing neurophysiologic assessments, including assessing the health of the spinal cord before, during and/or after surgery, and performing pedicle integrity assessments (screw test), nerve proximity and nerve direction to surgical instruments employed in accessing a surgical target site (nerve detection), and nerve pathology monitoring (nerve root retraction).

According to a broad aspect, the present invention includes a neuromonitoring system, comprising a control unit and a surgical instrument. The control unit has at least one of computer programming software, firmware and hardware capable of delivering a stimulation signal, receiving and processing neuromuscular responses due to the stimulation signal, and identifying a relationship between the neuromuscular response and the stimulation signal. The surgical instrument has at least one stimulation electrode electrically coupled to the control unit for transmitting a stimulation signal. The control unit is capable of assessing at least one of spinal cord health via MEP or SSEP monitoring, pedicle integrity, nerve proximity, and nerve pathology based on the identified relationship between a stimulation signal and a corresponding neuromuscular response. The control unit is equipped to communicate at least one of alpha-numeric and graphical information to a user regarding at least one of MEP, SSEP, pedicle integrity, nerve proximity, nerve direction, and nerve pathology. The information communicated to the user may indicate a safety level associated with the identified relationship between the stimulation signal and the corresponding neuromuscular response. The relationship identified may be the lowest or threshold current level required to evoke a significant neuromuscular response. The safety level may be determined based on a set of predetermined ranges related to the threshold current level.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIGS. 39A-39C are graphs illustrating use of the threshold hunting algorithm of FIG. 7 and further omitting stimulations when the likely result is already clear from previous data;

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems and methods disclosed herein boast a variety of inventive features and components that warrant patent protection, both individually and in combination.

Figure 1:
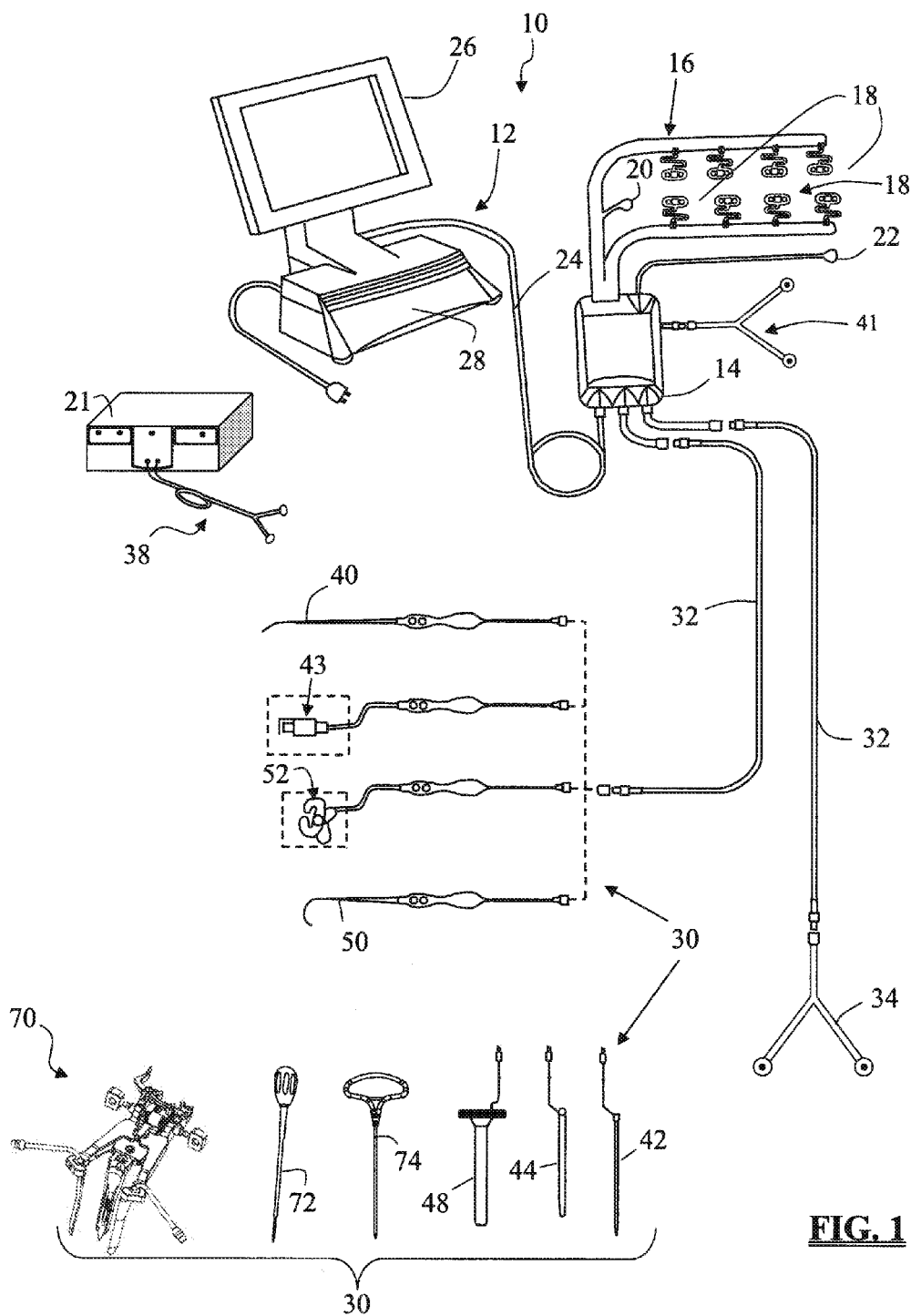
FIG. 1 is a perspective view of an exemplary neuromonitoring system 10 capable of performing neurophysiologic assessments such as for example, detecting pedicle breaches, nerve proximity (detection), nerve pathology, neuromuscular pathway status, and spinal cord health.

The present invention is directed at performing and monitoring neurophysiologic assessments before, during, and/or after surgery. FIG. 1 illustrates, by way of example only, a neuromonitoring system 10 capable of carrying out neurophysiologic assessment functions including, but not necessarily limited to, Twitch Test (neuromuscular pathway assessment), Screw Test (pedicle integrity testing), Detection (nerve proximity testing during surgical access), Nerve Retractor (nerve pathology monitoring), MEP (Motor Evoked Potential spinal cord monitoring), and SSEP (Somatosensory Evoked Potential spinal cord monitoring). It is expressly noted that, although described herein largely in terms of use in spinal surgery, the neuromonitoring system 10 and related methods of the present invention are suitable for use in any number of additional surgical procedures where neurological impairment is a concern.

The neuromonitoring system 10 includes a control unit 12, a patient module 14, an EMG harness 16, including eight pairs of EMG electrodes 18 and a return electrode 22 coupled to the patient module 14, and one or more of a host of surgical accessories 30 capable of being coupled to the patient module via accessory cables 32. Additional components may include, a pair of peripheral nerve stimulation (PNS) electrodes (one positive and one negative) 34 also coupled to the patient module 14 and an MEP stimulator 21 including a pair of stimulation electrodes 38. The surgical accessories 30 may include, but are not necessarily limited to, devices for performing pedicle screw tests (such as a screw test probe 40), surgical access components (such as a K-wire 42, one or more dilating cannula 44, a working cannula 48), and neural pathology monitoring devices (such as a nerve root retractor 50).

Figure 2:
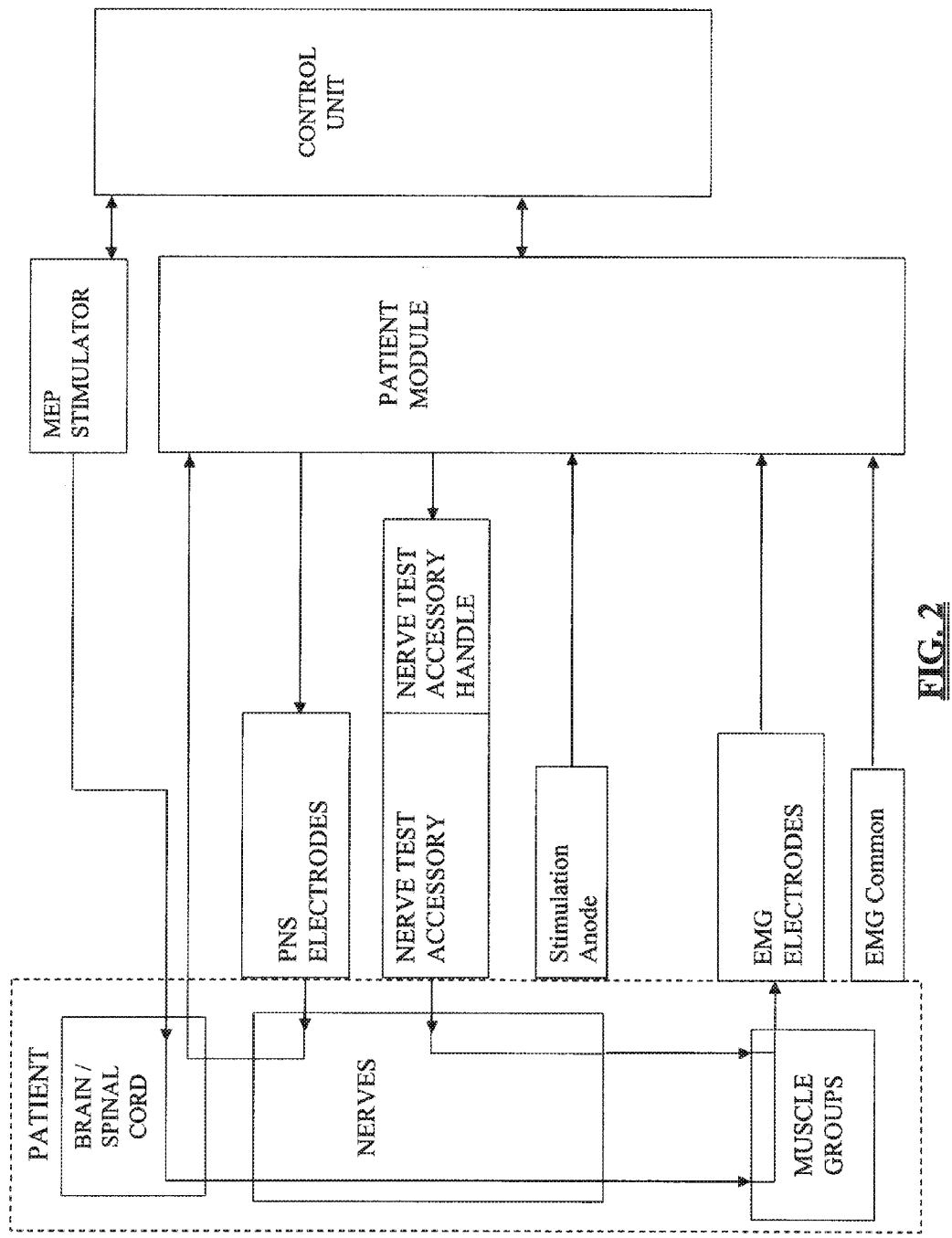
FIG. 2 is a block diagram of the neuromonitoring system 10 shown in FIG. 1.

A block diagram of the neuromonitoring system 10 is shown in FIG. 2, the operation of which is readily apparent in view of the following description. The control unit 12 includes a touch screen display 26 and a base 28, which collectively contain the essential processing capabilities for controlling the neuromonitoring system 10. The touch screen display 26 is preferably equipped with a graphical user interface (GUI) capable of communicating information to the user and receiving instructions from the user. The base 28 contains computer hardware and software that commands the stimulation sources, receives digitized signals and other information from the patient module 14, processes the EMG responses, displays the processed data to the operator via the display 26, and enables network connectivity. The primary functions of the software within the control unit 12 include receiving user commands via the touch screen display 26, activating stimulation in the requested mode (neuromuscular pathway assessment, screw test, nerve proximity, nerve direction, nerve pathology), processing signal data according to defined algorithms (described below), displaying received parameters and processed data, monitoring system status, and communicating with a remote client.

The patient module 14 is connected via a data cable 24 to the control unit 12, and contains the electrical connections to all electrodes, signal conditioning circuitry, stimulator drive and steering circuitry, and a digital communications interface to the control unit 12. In use, the control unit 12 is situated outside but close to the surgical field (such as on a cart adjacent the operating table) such that the display 26 is directed towards the surgeon for easy visualization. The patient module 14 should be located between the patient's legs, or may be affixed to the end of the operating table at mid-leg level using a bedrail clamp. The position selected should be such that the EMG leads can reach their farthest desired location without tension during the surgical procedure. MEP stimulator 21 is connected to the control unit 12 via a data cable, or preferably a wireless connection may be employed. MEP stimulator 21 includes a high voltage transformer and signal conditioning circuitry (not shown), for delivering the high voltage output stimulation signal required for MEP. MEP stimulator is preferably positioned near the control unit 12 and may be fashioned with a mount or hook (not shown) and hung from the surgical table, an IV pole near the patient's head, or other equipment positioned near the patient.

The information displayed to the user on the display 26 may include, but is not necessarily limited to, alpha-numeric and/or graphical information regarding any of the requested modes (e.g., MEP, SSEP, Twitch Test, Free-Run EMG, Screw Test (Basic, Difference, Dynamic), Detection, and Nerve Retractor), myotome/EMG levels, stimulation levels, etc. . . . In one embodiment, set forth by way of example only, this information may include at least some of the following components (depending on the active mode) as set forth in Table 1:

TABLE 1

| Screen Component | Description |
|---|---|
| Spine Image | An image of the human body/skeleton showing the electrode placement on the body, with labeled channel number tabs on each side (1-4 on the left and right). Left and right labels will show the patient orientation. The channel number tabs may be highlighted or colored depending on the specific function being performed. |
| Myotome & Level Names | A label to indicate the Myotome name and corresponding Spinal Level(s) associated with the channel of interest. |
| Menu | A drop down navigation component for toggling between functions. |
| Display Area | Shows procedure-specific information including stimulation results. |
| Color Indication | Enhances stimulation results with a color display of green, yellow, or red corresponding to the relative safety level determined by the system. |
| Mode Indicator | Graphics and/or name to indicate the currently active mode (MEP Auto, MEP Manual, SSEP, Twitch Test, Free-Run EMG, Basic Screw Test, Dynamic Screw Test, Difference Screw Test, Detection, Nerve Retractor). In an alternate embodiment, Graphics and/or name may also be displayed to indicate the instrument in use, such as the dilator, K-wire, retractor blades, screw test instruments, and associated size information, if applicable, of the cannula, with the numeric size. If no instrument is in use, then no indicator is displayed. |
| Stimulation Bar | A graphical stimulation indicator depicting the present stimulation status (i.e. on or off and stimulation current level) |
| Sequence Bar | Shows the last seven stimulation results and provides for annotation of results. |
| EMG waveforms | EMG waveforms may be optionally displayed on screen along with the stimulation results. |

Figure 3:
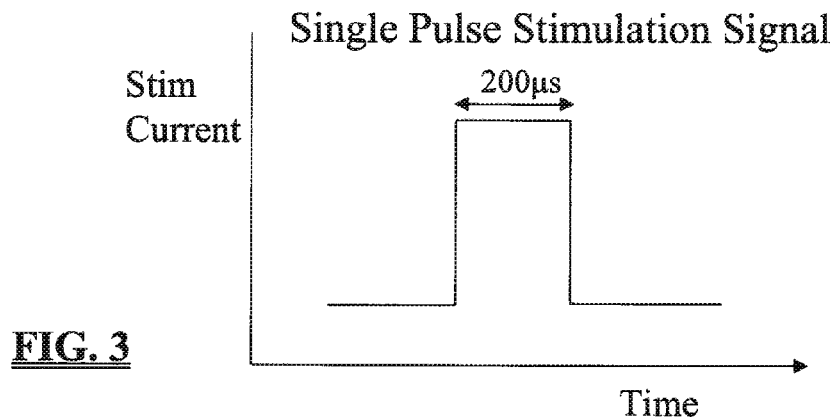
FIG. 3 is a graph illustrating an exemplary single pulse stimulation signal according to one embodiment of the present invention.
Figure 4:
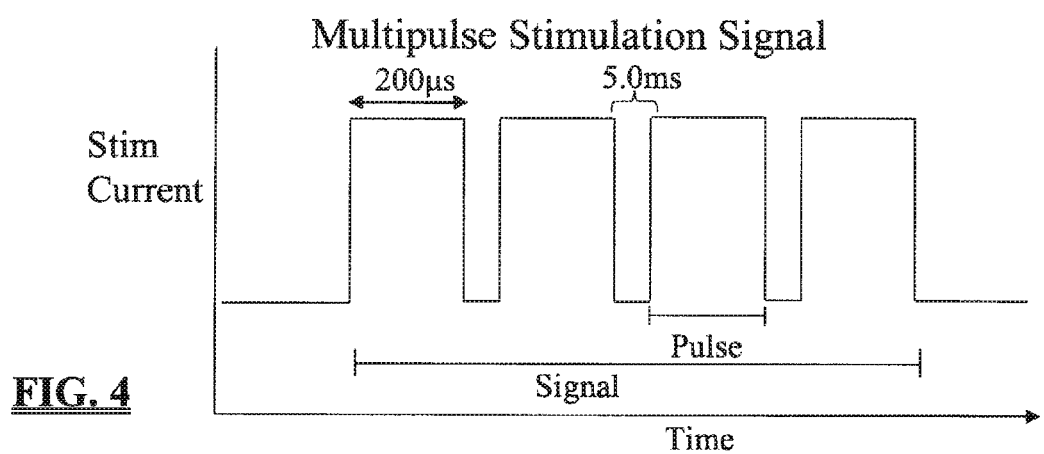
FIG. 4 is a is a graph illustrating an exemplary multipulse stimulation signal according to one embodiment of the present invention.
Figure 5:
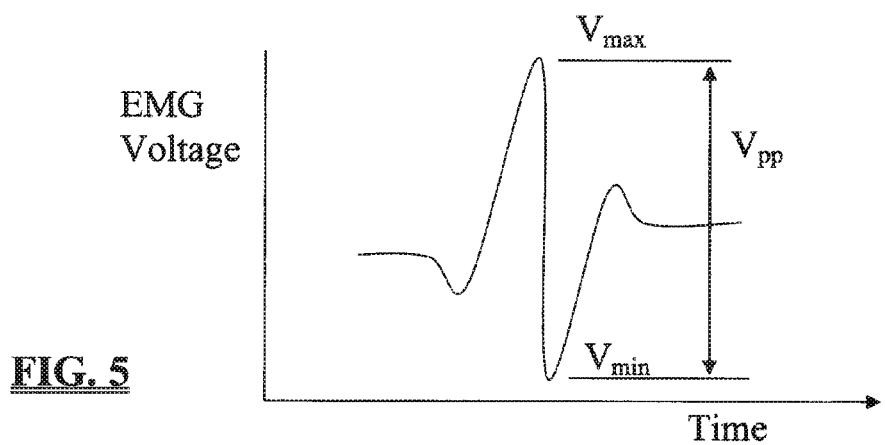
FIG. 5 is a graph illustrating an exemplary EMG response to the stimulus of FIG. 3 or 4.

The neuromonitoring functionality of the neuromonitoring system 10 (except SSEP, which will be described below) is based on assessing the evoked response of the various muscles myotomes monitored by the system 10 in relation to a stimulation signal transmitted by the system 10 (via patient module 14 or MEP stimulator 21). This is best shown in FIGS. 3-5, wherein FIG. 5 illustrates the resulting EMG of a monitored myotome in response to one of the exemplary stimulation signals shown in FIG. 3 and FIG. 4. The EMG responses provide a quantitative measure of the nerve depolarization caused by the electrical stimulus.

In one embodiment, EMG response monitoring is accomplished via 8 pairs EMG electrodes 18 (placed on the skin over the muscle groups to be monitored), a common electrode 20 providing a ground reference to pre-amplifiers in the patient module 14, and an anode electrode 22 providing a return path for the stimulation current. It should be appreciated that any of a variety of known electrodes can be employed, including but not limited to surface pad electrodes and needle electrodes. It should also be appreciated that EMG electrode placement depends on a multitude of factors, including for example, the spinal cord level and particular nerves at risk and user preference, among others. In one embodiment (set forth by way of example only), the preferred EMG configuration is described for Lumbar surgery in Table 2, Thoracolumbar surgery in Table 3, and Cervical surgery in Table 4 below:

TABLE 2

Lumbar

| Color | Channel | Myotome | Nerve | Spinal Level |
|---|---|---|---|---|
| Red | Right 1 | Right Vastus Medialis | Femoral | L2, L3, L4 |
| Orange | Right 2 | Right Tibialis Anterior | Common Peroneal | L4, L5 |
| Yellow | Right 3 | Right Biceps Femoris | Sciatic | L5, S1, S2 |
| Green | Right 4 | Right Medial Gastroc. | Post Tibial | S1, S2 |
| Blue | Left 1 | Left Vastus Medialis | Femoral | L2, L3, L4 |
| Violet | Left 2 | Left Tibialis Anterior | Common Peroneal | L4, L5 |
| Gray | Left 3 | Left Biceps Femoris | Sciatic | L5, S1, S2 |
| White | Left 4 | Left Medial Gastroc. | Post Tibial | S1, S2 |

TABLE 3

Thoracolumbar

| Color | Channel | Myotome | Nerve | Spinal Level |
| --- | --- | --- | --- | --- |
| Red | Right 1 | Right Abductor Pollicis Brevis | Median | C6, C7, C8, T1 |
| Orange | Right 2 | Right Vastus Medialis | Femoral | L2, L3, L4 |
| Yellow | Right 3 | Right Tibialis Anterior | Common Peroneal | L4, L5 |
| Green | Right 4 | Right Abductor Hallucis | Tibial | L4, L5, S1 |
| Blue | Left 1 | Left Abductor Pollicis Brevis | Median | C6, C7, C8, T1 |
| Violet | Left 2 | Left Vastus Medialis | Femoral | L2, L3, L4 |
| Gray | Left 3 | Left Tibialis Anterior | Common Peroneal | L4, L5 |
| White | Left 4 | Left Abductor Hallucis | Tibial | L4, L5, S1 |

TABLE 4

Cervical

| Color | Channel | Myotome | Nerve | Spinal Level |
| --- | --- | --- | --- | --- |
| Red | Right 1 | Right Deltoid | Axilliary | C5, C6 |
| Orange | Right 2 | Right Flexor Carpi Radialis | Median | C6, C7, C8 |
| Yellow | Right 3 | Right Abductor Pollicis Brevis | Median | C6, C7, C8, T1 |
| Green | Right 4 | Right Abductor Hallucis | Tibial | L4, L5, S1 |
| Blue | Left 1 | Left Deltoid | Axilliary | C5, C6 |
| Violet | Left 2 | Left Flexor Carpi Radialis | Median | C6, C7, C8 |
| Gray | Left 3 | Left Abductor Pollicis Brevis | Median | C6, C7, C8, T1 |
| White | Left 4 | Left Abductor Hallucis | Tibial | L4, L5, S1 |

Figure 6:
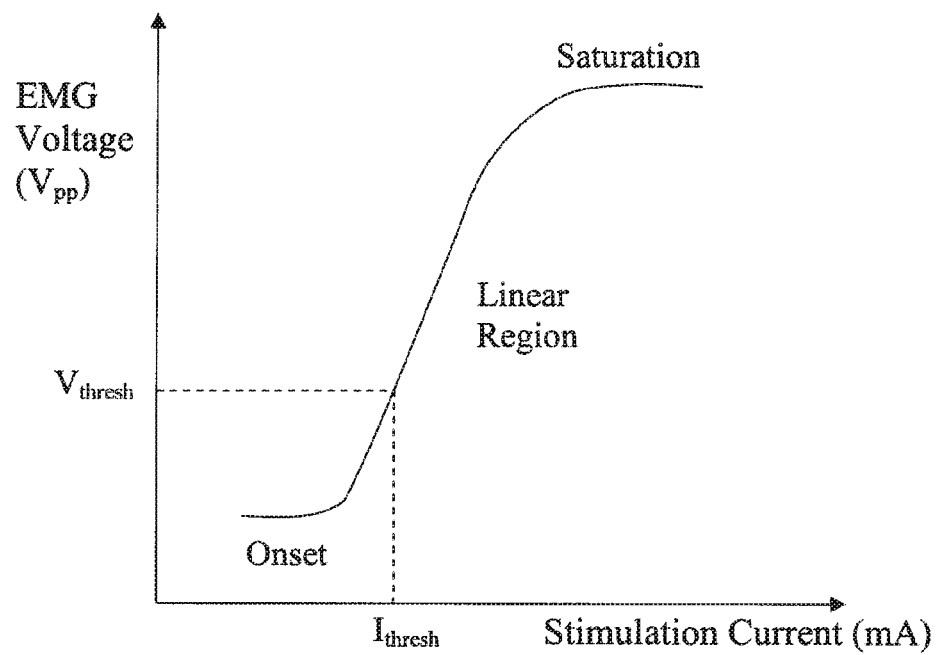
FIG. 6 is a graph illustrating a plot of peak-to-peak voltage (Vpp) for each given stimulation current level ($I_{Stim}$) forming a stimulation current pulse train according to the present invention (otherwise known as a "recruitment curve")

A basic premise underlying the methods employed by the system 10 for much of the neurophysiologic monitoring is that neurons and nerves have characteristic threshold current levels ($I_{Thresh}$) at which they will depolarize, resulting in detectable muscle activity. Below this threshold current, stimulation signals will not evoke a significant EMG response. Each EMG response can be characterized by a peak-to-peak voltage of $V_{pp}=V_{max}-V_{min}$, shown in FIG. 5. Once the stimulation threshold ($I_{Thresh}$) is reached, the evoked response is reproducible and increases with increasing stimulation until saturation is reached as shown in FIG. 6. This is known as a "recruitment curve." In one embodiment, a significant EMG response is defined as having a $V_{pp}$ of approximately 100 uV. The lowest stimulation signal current that evokes this threshold voltage ($V_{Thresh}$) is called $I_{Thresh}$. $I_{thresh}$ increases as the degree of electrical communication between a stimulation signal and a nerve decreases and conversely, $I_{thresh}$ decreases as the electrical communication increases between the nerve and stimulation pulse. Thus monitoring $I_{thresh}$ can provide the surgeon with useful information about neurological related issues. By way of example, an excessively high $I_{thresh}$ or an increase over a previous measurement during MEP may indicate a problem in the spinal cord inhibiting transmission (communication) of the stimulation signal to the nerve. An excessively high $I_{thresh}$ or an increase over a previous measurement during nerve retractor mode may indicate a deterioration of nerve root function caused by over retraction. During screw test and detection modes a low $I_{thresh}$ value may indicate a breach in the pedicle allowing the electrical signal to escape the pedicle, or the close proximity of a nerve, respectively. Armed with the useful information conveyed by $I_{thresh}$, the surgeon may detect a problem or potential problem early and then act to avoid and/or mitigate the problem.

In one embodiment, the value of $I_{thresh}$ is displayed to the surgeon along with a color code so that the surgeon may easily comprehend the situation and avoid neurological impairment to the patient. The colors Red, Yellow, and Green may preferably be displayed (by way of example only) along with $I_{thresh}$ and/or other function specific data. Red maybe used to indicate an unsafe $I_{thresh}$ level. By way of example, during screw testing and nerve detection, an unsafe or "Red" level occurs when the $I_{thresh}$ falls below a predetermined value. During pathology monitoring, for example only, the unsafe level occurs when $I_{thresh}$ rises above a predetermined value. The "Green" or safe level may indicate to the surgeon that there is little danger in continuing with the procedure. By way of example only, the color green may be displayed during screw testing and nerve detection when the $I_{thresh}$ value is greater than a predetermined value. The converse is again true for nerve pathology monitoring, and green may indicate that $I_{thresh}$ is below a predetermined level. The "Yellow" or cautionary level may be used to indicate that $I_{thresh}$ falls in between the predetermined safe and unsafe levels. EMG channel tabs on the display may be selected via the touch screen display 26 to show the $I_{thresh}$ and/or color safety level of the nerve corresponding to a given tab. Additionally, the EMG channel possessing the least desirable (e.g. lowest) $I_{thresh}$ may be automatically highlighted and/or colored to clearly indicate this fact to the user.

By way of example only, the various functional modes of the neuromonitoring system 10 may include the Twitch Test, Free-run EMG, Basic Screw Test, Difference Screw Test, Dynamic Screw Test, MaXcess® Detection, Nerve Retractor, MEP Auto, MEP manual, and SSEP modes, all of which will be described briefly below. The Twitch Test mode is designed to assess the neuromuscular pathway via the so-called "train-of-four test" test to ensure the neuromuscular pathway is free from muscle relaxants prior to performing neurophysiology-based testing, such as bone integrity (e.g. pedicle) testing, nerve detection, and nerve retraction. This is described in greater detail within PCT Patent App. No. PCT/US2005/036089, entitled "System and Methods for Assessing the Neuromuscular Pathway Prior to Nerve Testing," filed Oct. 7, 2005, the entire contents of which is hereby incorporated by reference as if set forth fully herein. The Basic Screw Test, Difference Screw Test, and Dynamic Screw Test modes are designed to assess the integrity of bone (e.g. pedicle) during all aspects of pilot hole formation (e.g., via an awl), pilot hole preparation (e.g. via a tap), and screw introduction (during and after). These modes are described in greater detail in. PCT Patent App. No. PCT/US02/35047 entitled "System and Methods for Performing Percutaneous Pedicle Integrity Assessments," filed on Oct. 30, 2002, and PCT Patent App. No. PCT/US2004/025550, entitled "System and Methods for Performing Dynamic Pedicle Integrity Assessments," filed on Aug. 5, 2004 the entire contents of which are both hereby incorporated by reference as if set forth fully herein. The MaXcess® Detection mode is designed to detect the presence of nerves during the use of the various surgical access instruments of the neuromonitoring system 10, including the k-wire 42, dilator 44, cannula 46, retractor assembly 70. This mode is described in greater detail within PCT Patent App. No. PCT/US2002/22247, entitled "System and Methods for Determining Nerve Proximity, Direction, and Pathology During Surgery," filed on Jul. 11, 2002, the entire contents of which is hereby incorporated by reference as if set forth fully herein. The Nerve Retractor mode is designed to assess the health or pathology of a nerve before, during, and after retraction of the nerve during a surgical procedure. This mode is described in greater detail within PCT Patent App. No. PCT/

US2002/30617, entitled "System and Methods for Performing Surgical Procedures and Assessments," filed on Sep. 25, 2002, the entire contents of which are hereby incorporated by reference as if set forth fully herein. The MEP Auto and MEP Manual modes are designed to test the motor pathway to detect potential damage to the spinal cord by stimulating the motor cortex in the brain and recording the resulting EMG response of various muscles in the upper and lower extremities. The SSEP function is designed to test the sensory pathway to detect potential damage to the spinal cord by stimulating peripheral nerves inferior to the target spinal level and recording the action potential from sensors superior to the spinal level. The MEP Auto, MEP manual, and SSEP modes are described in greater detail within PCT Patent App. No. PCT/US2006/003966, entitled "System and Methods for Performing Neurophysiologic Assessments During Spine Surgery," filed on Feb. 2, 2006, U.S. patent Ser. No. 12/080,630, entitled "Neurophysiologic Monitoring System," filed on Apr. 3, 2008, and PCT Patent App. No. PCT/US2009/05650, entitled "Neurophysiologic Monitoring System and Related Methods," and filed on Oct. 15, 2009, the entire contents of which are each hereby incorporated by reference as if set forth fully herein. These functions will be explained now in brief detail.

Figure 7:
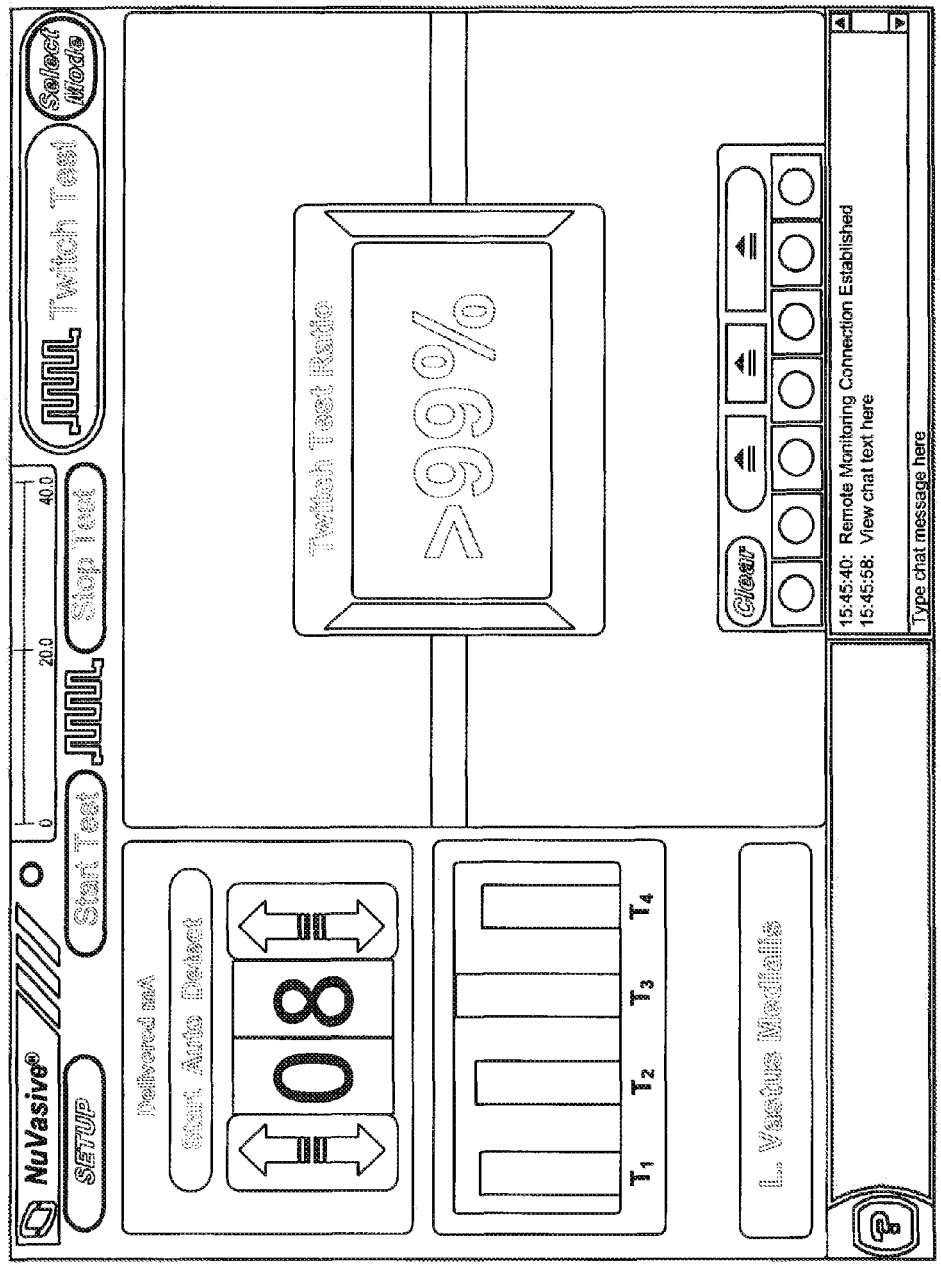
FIG. 7 is an exemplary screen display illustrating one embodiment of the Twitch Test mode for performing neuromuscular pathway assessments.

The neuromonitoring system 10 performs neuromuscular pathway (NMP) assessments, via Twitch Test mode, by electrically stimulating a peripheral nerve via PNS electrodes 34 placed on the skin over the nerve or by direct stimulation of a spinal nerve using a surgical accessory such as screw test probe 40 Evoked responses from the muscles innervated by the stimulated nerve are detected and recorded, the results of which are analyzed and a relationship between at least two responses or a stimulation signal and a response is identified. The identified relationship provides an indication of the current state of the NMP. The identified relationship may include, but is not necessarily limited to, one or more of magnitude ratios between multiple evoked responses and the presence or absence of an evoked response relative to a given stimulation signal or signals. Details of the test indicating the state of the NMP and the relative safety of continuing on with nerve testing are conveyed to the surgeon via the screen display 26, as illustrated in the exemplary screen view depicted in FIG. 7

The neuromonitoring system 10 may test the integrity of pedicle holes (during and/or after formation) and/or screws (during and/or after introduction) via the Basic Screw test, Difference Screw Test, and/or Dynamic Screw Test modes. For the Basic Screw Test a screw test probe 40 is placed in the screw hole prior to screw insertion or placed on the installed screw head and a stimulation signal is applied. The insulating character of bone will prevent the stimulation current, up to a certain amplitude, from communicating with the nerve, thus resulting in a relatively high $I_{thresh}$, as determined via the basic threshold hunting algorithm described below. However, in the event the pedicle wall has been breached by the screw or tap, the current density in the breach area will increase to the point that the stimulation current will pass through to the adjacent nerve roots and they will depolarize at a lower stimulation current, thus $I_{thresh}$ will be relatively low. The system described herein may exploit this knowledge to inform the practitioner of the current $I_{thresh}$ of the tested screw to determine if the pilot hole has breached the pedicle wall.

In Dynamic Screw Test mode, screw test probe 40 may be replaced with an electric coupling device 43, 52 which may be utilized to couple a surgical tool, such as for example, a tap member 72 or a bone awl 74, to the neuromonitoring system 10. In this manner, a stimulation signal may be passed through the surgical tool and pedicle integrity testing can be performed while the tool is in use. Thus, screw testing may be performed during pilot hole formation by coupling the bone awl 74 to the neuromonitoring system 10 and during pilot hole preparation by coupling the tap 72 to the system 10 Likewise, by coupling a pedicle screw to the neuromonitoring system 10 (such as via pedicle screw instrumentation), screw testing may be performed during screw introduction.

In the Difference Screw Test mode, a baseline threshold value is determined by directly stimulating a nerve. After establishing the baseline threshold the screw or pilot hole is stimulated and the threshold result is compared to the baseline result, and the difference value is used to represent the relative safety level.

Figure 8:
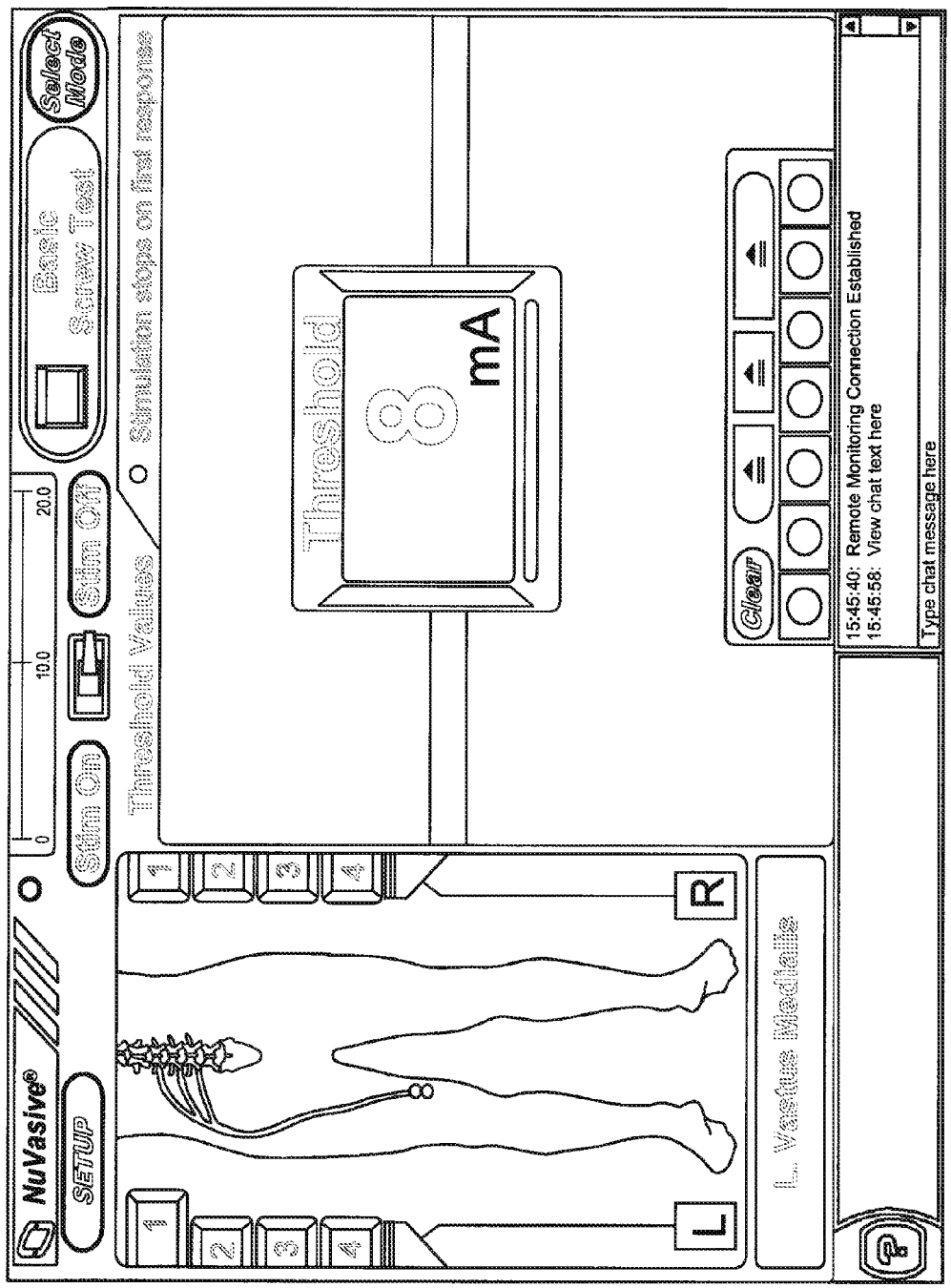
FIG. 8 is an exemplary screen display illustrating one embodiment of the Basic Screw Test mode for performing pedicle integrity assessments.
Figure 9:
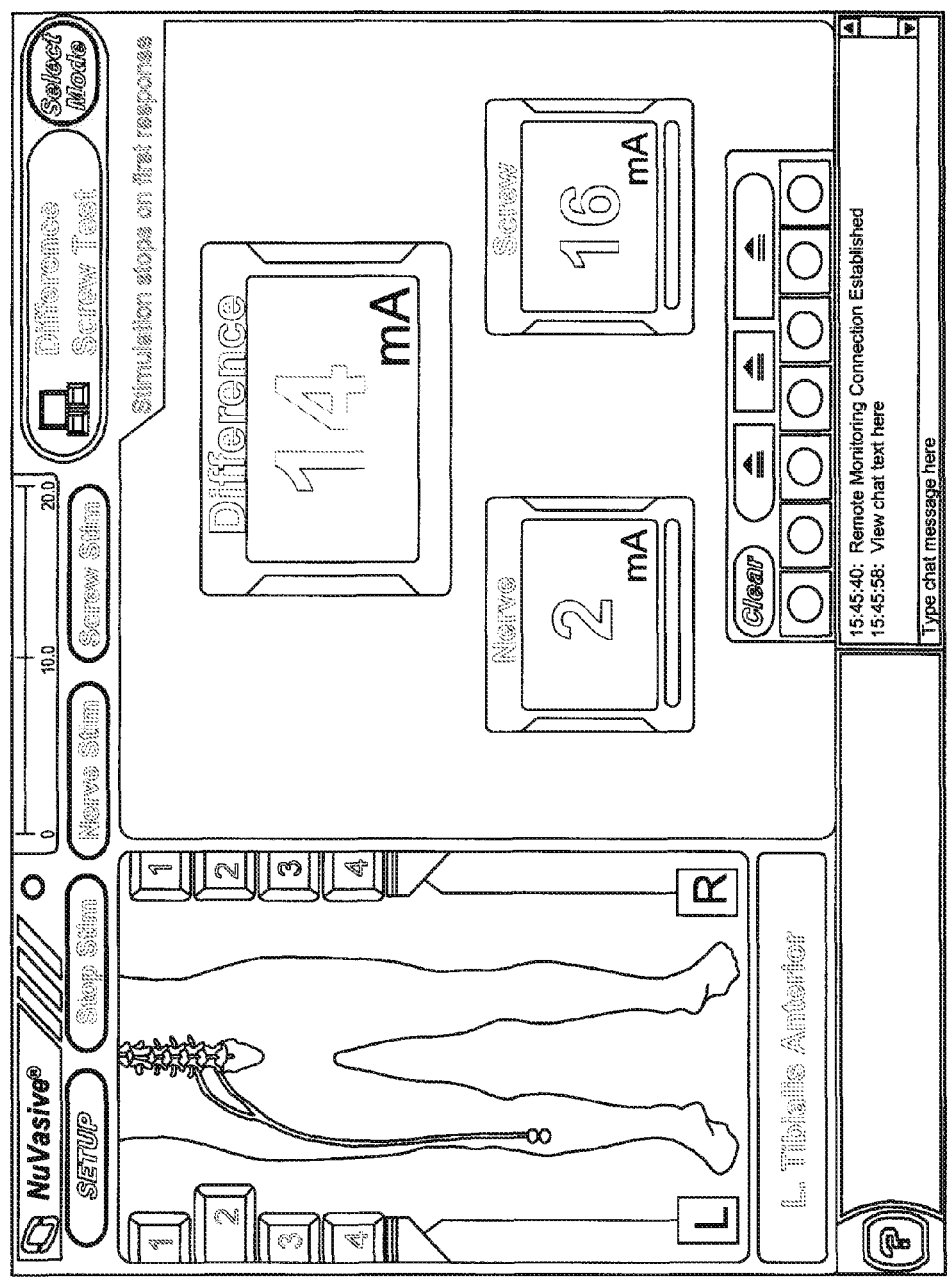
FIG. 9 is an exemplary screen display illustrating one embodiment of the Difference Screw Test mode for performing pedicle integrity assessments.
Figure 10:
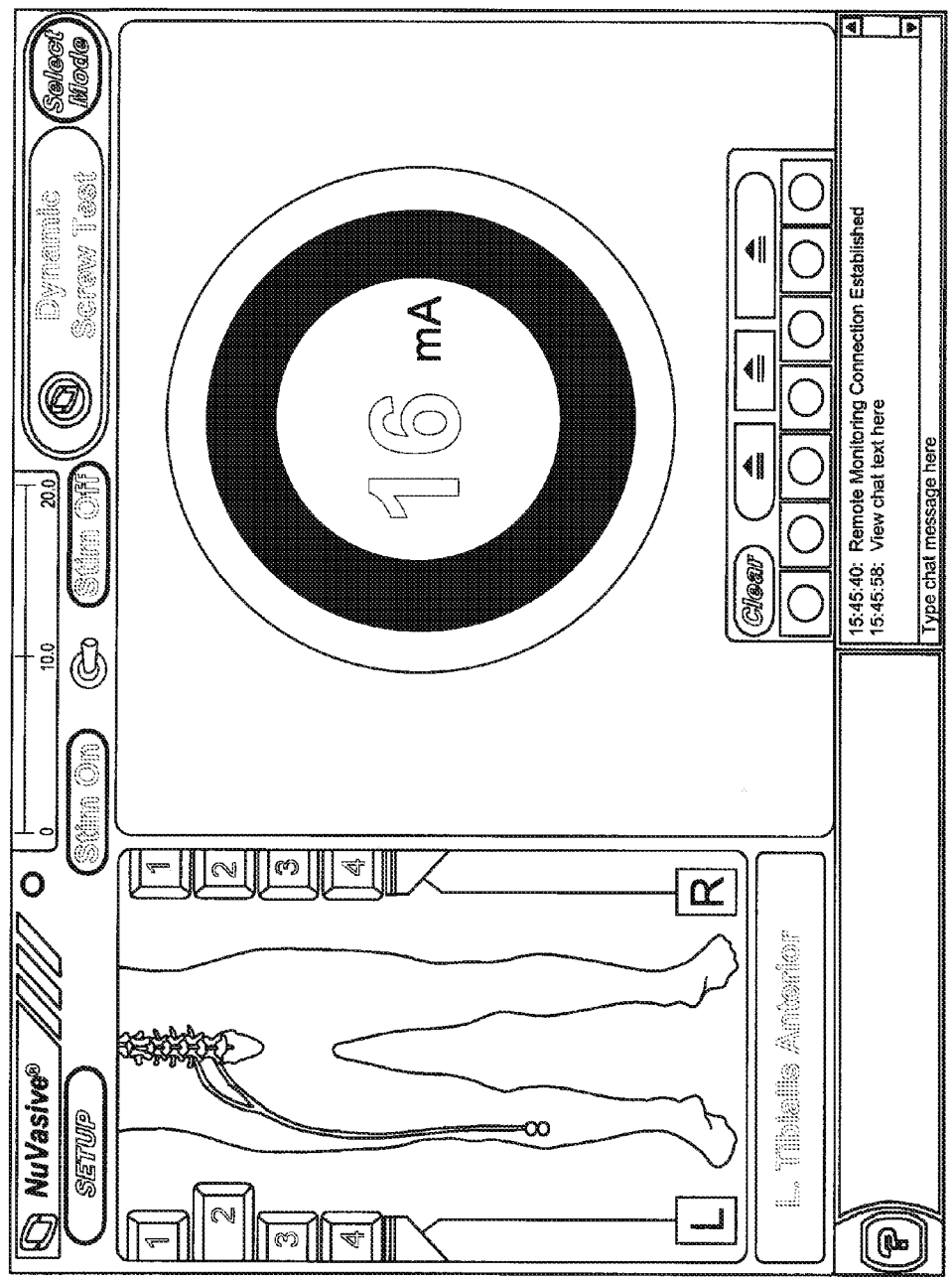
FIG. 10 is an exemplary screen display illustrating one embodiment of the Dynamic Screw Test mode for performing pedicle integrity assessments.

Stimulation results (including but not necessarily limited to at least one of the numerical $I_{thresh}$ value and color coded safety level indication) and other relevant data are conveyed to the user on display 26, as illustrated in FIGS. 8-10. FIG. 8 is an exemplary screen view of the Basic Screw Test embodiment. FIG. 9 illustrates an exemplary screen view of the Difference Screw Test embodiment. FIG. 10 is an exemplary screen view of the Dynamic Screw Test embodiment. In one embodiment of the various screw test functions (e.g. Basic, Dynamic, and Difference), green corresponds to a threshold range of 9 milliamps (mA) or greater, a yellow corresponds to a stimulation threshold range of 6-8 mA, and a red corresponds to a stimulation threshold range of 6 mA or below. EMG channel tabs may be selected via the touch screen display 26 to show the $I_{thresh}$ of the corresponding nerves. Additionally, the EMG channel possessing the lowest $I_{thresh}$ may be automatically highlighted and/or colored to clearly indicate this fact to the user.

Figure 11:
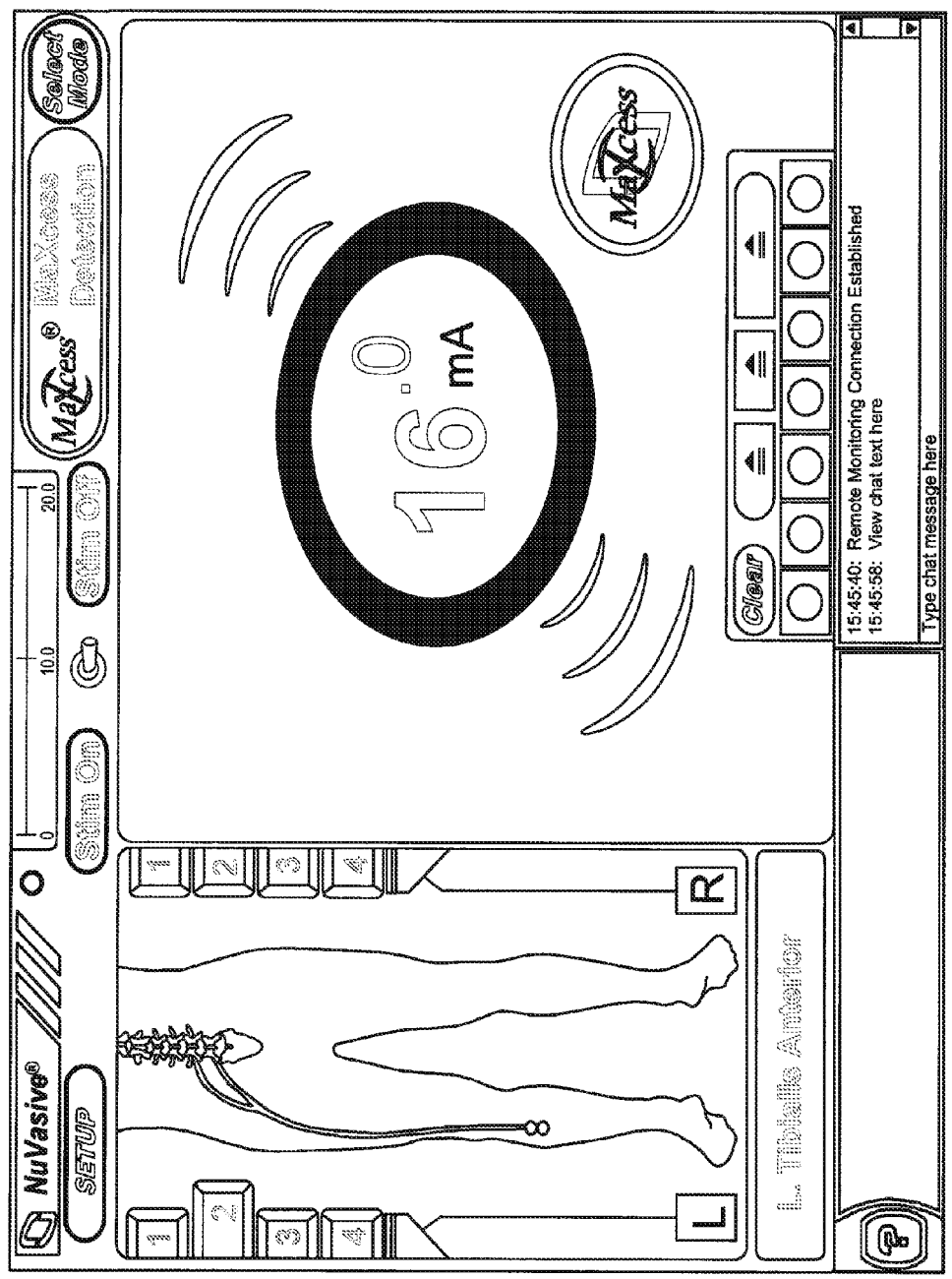
FIG. 11 is an exemplary screen display illustrating one embodiment of the MaXcess® (Surgical Access) Detection mode for performing nerve proximity assessments.

The neuromonitoring system 10 may perform nerve proximity testing, via the MaXcess® Detection mode, to ensure safe and reproducible access to surgical target sites. Using the surgical access components 42-46, the system 10 detects the existence of neural structures before, during, and after the establishment of an operative corridor through (or near) any of a variety of tissues having such neural structures which, if contacted or impinged, may otherwise result in neural impairment for the patient. The surgical access components 42-46 are designed to bluntly dissect the tissue between the patient's skin and the surgical target site. Cannulae or dilators of increasing diameter, which are equipped with one or more stimulating electrodes, are advanced towards the target site until a sufficient operating corridor is established. As the cannulae or dilators are advanced to the target site electrical stimulation signals are emitted via the stimulation electrodes. The stimulation signal will stimulate nerves in close proximity to the stimulation electrode and the corresponding EMG response is monitored. As a nerve gets closer to the stimulation electrode, the stimulation current required to evoke a muscle response decreases because the resistance caused by human tissue will decrease, and it will take less current to cause nervous tissue to depolarize. $I_{thresh}$ is calculated, using the basic threshold hunting algorithm described above, providing a measure of the communication between the stimulation signal and the nerve and thus giving a relative indication of the proximity between access components and nerves. An illustrative example of a screen view for MaXcess Detection mode is depicted in FIG. 11. Preferably, a green or safe level corresponds to a stimulation threshold range of 10 milliamps (mA) or greater, a yellow level denotes a stimulation threshold range of 5-9 mA, and a red level denotes a stimulation threshold range of 4 mA or below. In a detector embodiment of the invention, a dynamic series of stimuli would be emitted to give the practitioner real time data on the proximity of the surgical instruments to the nerve.

Additional and/or alternative surgical access components such as, by way of example only, a tissue retraction assembly 70 may be coupled to the system 10 and employed to provide safe and reproducible access to a surgical target site. Tissue retraction assembly 70 and various embodiments and uses thereof have been shown and described co-pending and commonly assigned U.S. patent application Ser. No. 10/967,668, entitled "Surgical Access System and Related Methods," filed on Oct. 18, 2004, the entire contents of which are expressly incorporated by reference as if set forth herein in their entirety.

Figure 12:
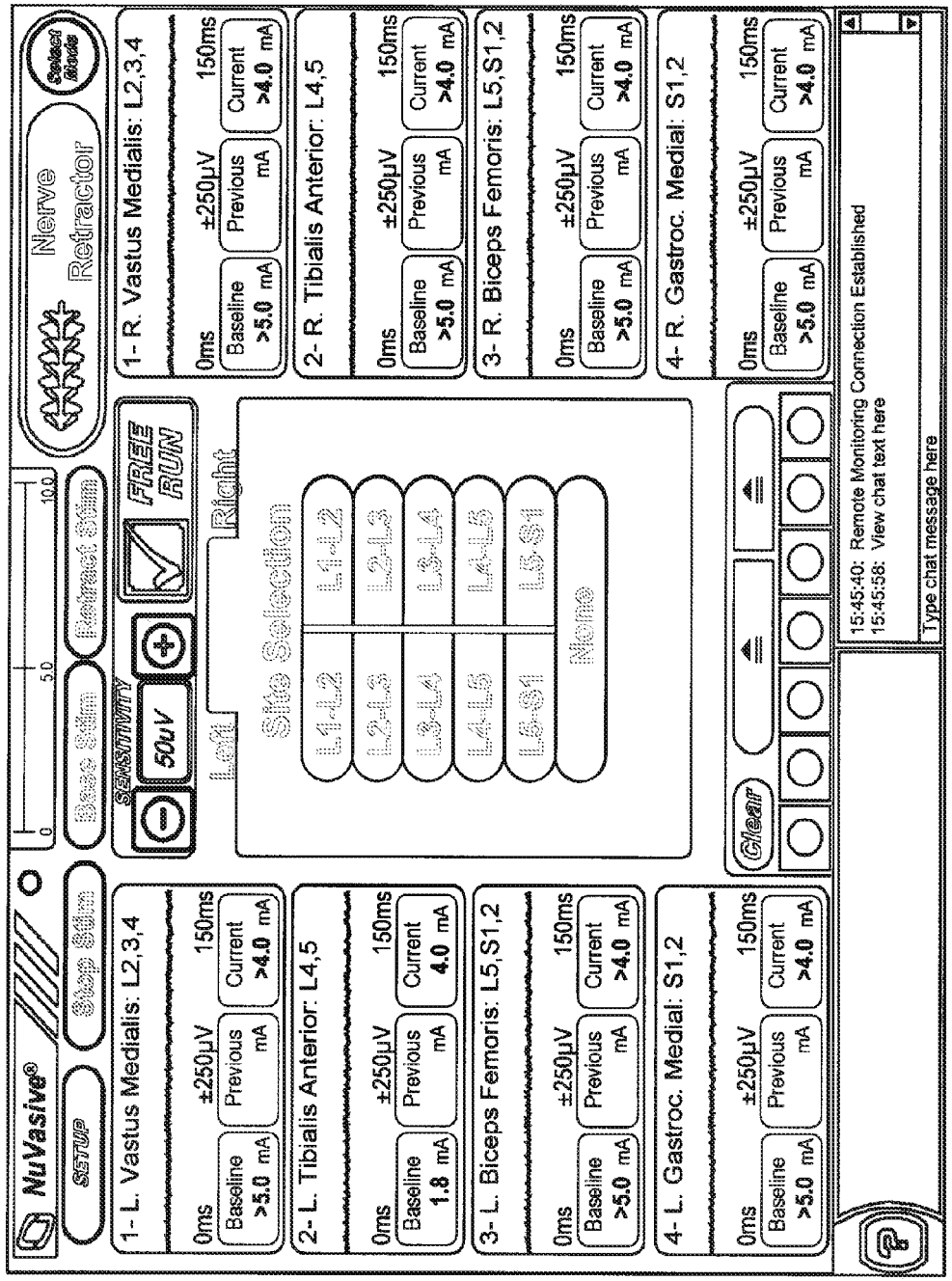
FIG. 12 is an exemplary screen display illustrating one embodiment of the Nerve Retractor mode for performing neural pathology monitoring.

The neuromonitoring system 10 preferably accomplishes neural pathology monitoring via the Nerve Retractor mode, specifically by determining a baseline stimulation threshold with direct contact between the nerve retractor 50 and the nerve, prior to retraction. Subsequent stimulation thresholds are determined during retraction and they are compared to the baseline threshold. Significant changes in the stimulation threshold may indicate potential trauma to the nerve caused by the retraction and are displayed to the user on the display 26. An increase in $I_{thresh}$ over time is an indication that the nerve function is deteriorating and retraction should be reduced or stopped altogether to prevent permanent damage. $I_{thresh}$ is preferably determined for each channel according to the multi-channel hunting algorithm described above. FIG. 12 shows an exemplary screen view of the Nerve Retractor mode according to the present invention.

Figure 13:
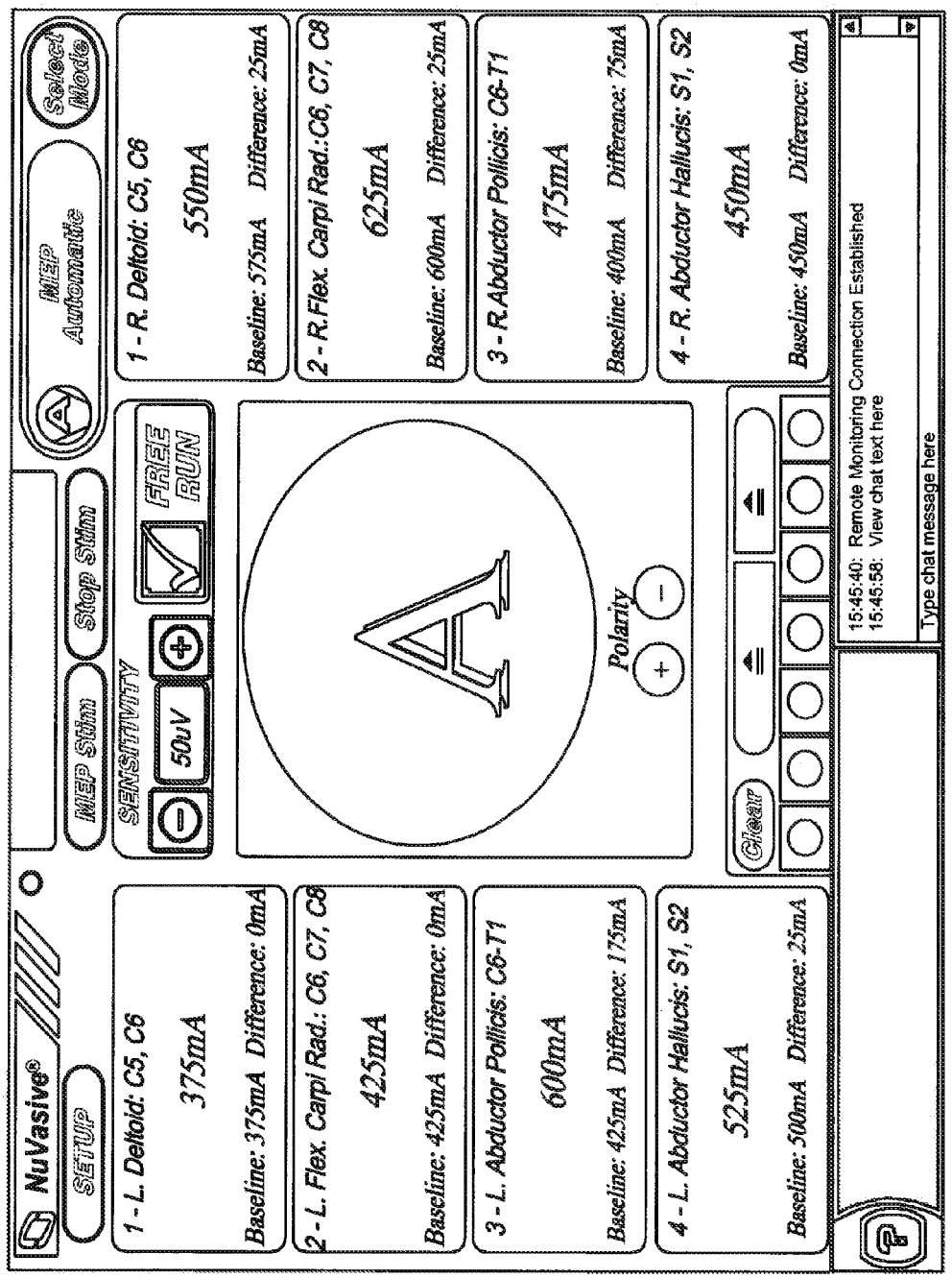
FIG. 13 is an exemplary screen display illustrating one embodiment of the MEP Auto mode for performing spinal cord assessments.
Figure 14:
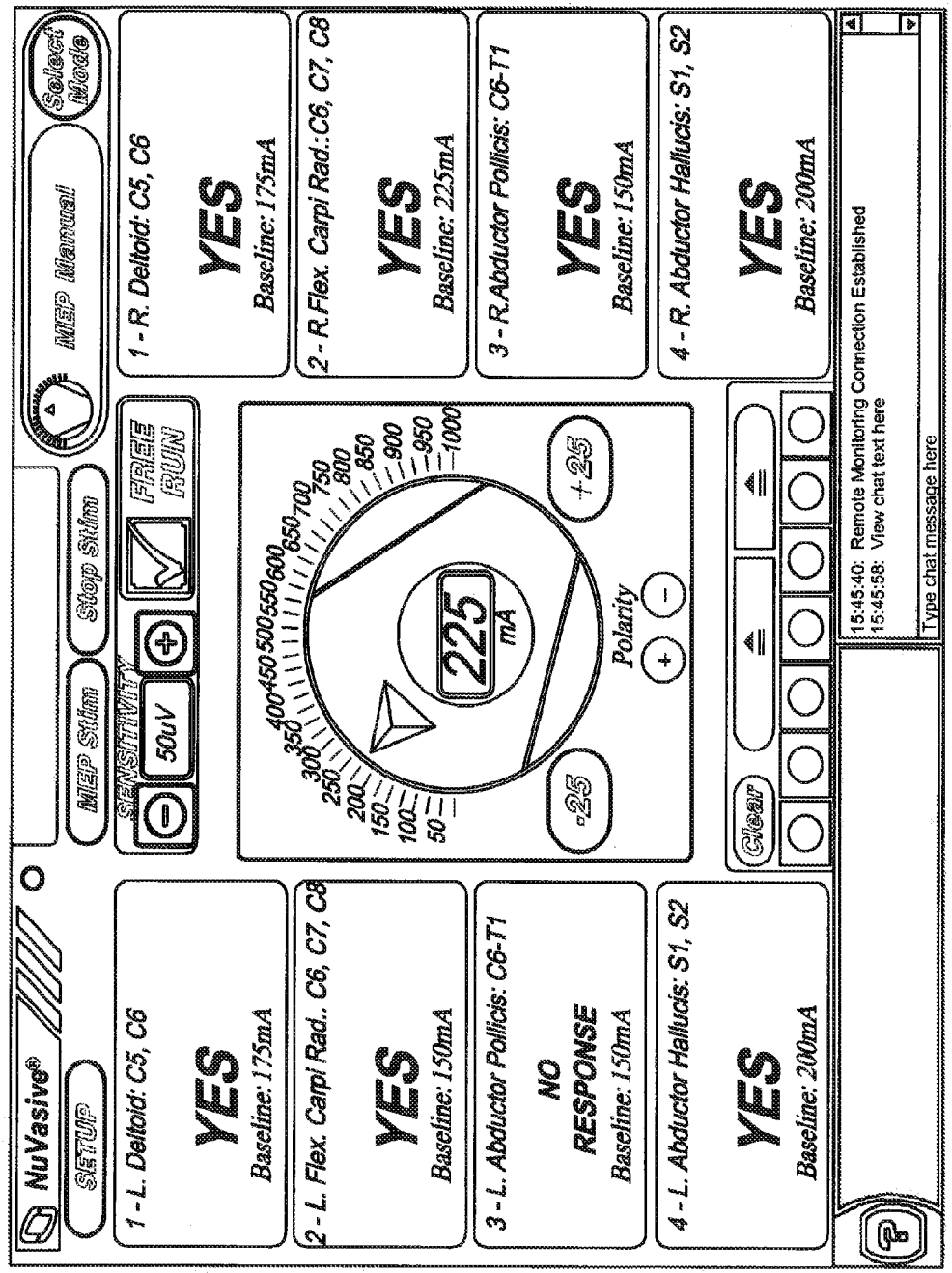
FIG. 14 is an exemplary screen display illustrating one embodiment of the MEP manual mode for performing spinal cord assessments.

The neuromonitoring system 10 performs assessments of spinal cord health using one or more of MEP Auto, MEP Manual, and SSEP modes. In MEP modes, stimulation signals are delivered to the Motor Cortex via MEP stimulator 21 and resulting EMG responses are detected from various muscles in the upper and lower extremities. An increase in $I_{thresh}$ from an earlier test to a later test may indicate a degradation of spinal cord function. Likewise, the absence of a significant EMG response to a given $I_{stim}$ on a channel that had previously reported a significant response to the same or lesser $I_{stim}$ is also indicative of a degradation in spinal cord function. These indicators are detected by the system in the MEP modes and reported to the surgeon. In MEP Auto mode the system determines the $I_{thresh}$ baseline for each channel corresponding to the various monitored muscles, preferably early in the procedure, using the multi-channel algorithm described. Throughout the procedure subsequent tests may be conducted to again determine $I_{thresh}$ for each channel. The difference between the resulting $I_{thresh}$ values and the corresponding baseline are computed by the system 10 and compared against predetermined "safe" and "unsafe" difference values. The $I_{thresh}$, baseline, and difference values are displayed to the user, along with any other indicia of the safety level determined (such as a red, yellow, green color code), on the display 26, as illustrated in FIG. 13. In MEP Manual mode, the user selects the stimulation current level and the system reports whether or not the stimulation signal evokes a significant response on each channel. Stimulation results may be shown on the display 26 in the form of "YES" and "No" responses, or other equivalent indicia, as depicted in FIG. 14. Using either mode the surgeon may thus be alerted to potential complications with the spinal cord and any corrective actions deemed necessary may be undertaken at the discretion of the surgeon.

Figure 15:
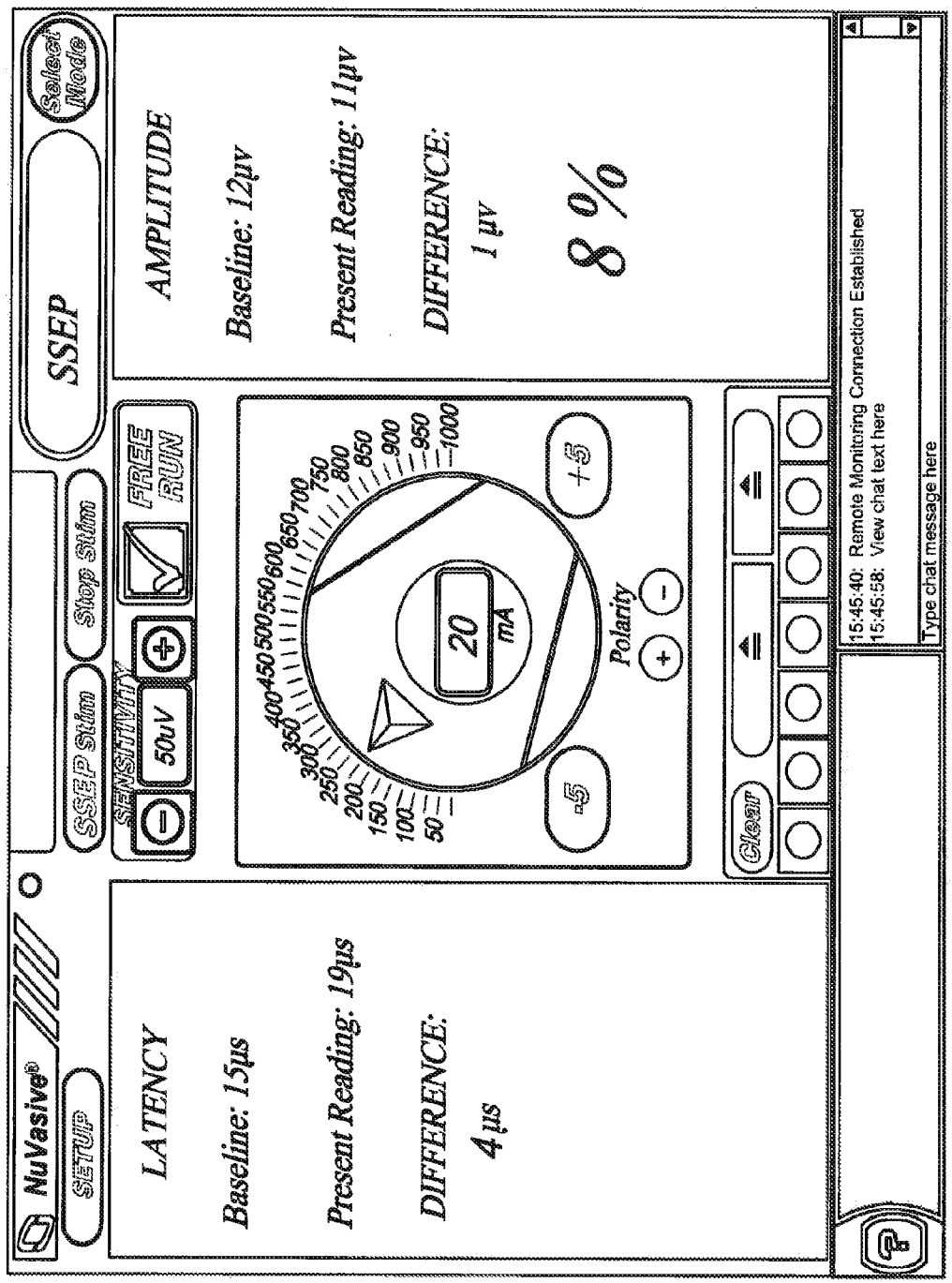
FIG. 15 is an exemplary screen display illustrating one embodiment of the SSEP mode for performing spinal cord assessments.

In SSEP mode, the neuromonitoring system 10 stimulates peripheral sensory nerves that exit the spinal cord below the level of surgery and then measures the electrical action potential from electrodes located on the nervous system tract superior to the surgical target site. To accomplish this, peripheral nerve stimulation (PNS) electrodes 25 may be placed on the skin over the desired peripheral nerve (such as by way of example only, the Posterior Tibial nerve) and recording electrodes 41 are positioned on the recording sites (such as, by way of example only, the skin over the C2 vertebra, Cp3 scalp, Cp4 scalp, Erb's point, Popliteal Fossa) and stimulation signals are delivered from the patient module 14. Damage in the spinal cord may disrupt the transmission of the signal up along the spinothalamic pathway through the spinal cord resulting in a weakened, delayed, or absent signal at the recording sites superior to the surgery location (e.g. cortical and subcortical sites). To check for these occurrences, the system 10 monitors the amplitude and latency of the evoked signal response. According to one embodiment, the system 10 may perform SSEP in either of two modes: Automatic mode and Manual mode. In SSEP Auto mode, the system 10 compares the difference between the amplitude and latency of the signal response vs. the amplitude and latency of a baseline signal response. The difference is compared against predetermined "safe" and "unsafe" levels and the results are displayed on display 26, as seen in the exemplary screen view illustrated in FIG. 15. According to one embodiment, the system may determine safe and unsafe levels based on each of the amplitude and latency values for each of the cortical and subcortical sites individually, for each stimulation channel. That is, if either of the subcortical and cortical amplitudes decrease by a predetermined level, or either of the subcortical and cortical latency values increase by a predetermined level, the system may issue a warning. By way of example, the alert may comprise a Red, Yellow, Green type warning associated with the applicable channel wherein Red indicates that at least one of the determined values falls within the unsafe level, the color green may indicate that all of the values fall within the safe level, and the color yellow may indicate that at least one of the values falls between the safe and unsafe levels. To generate more information, the system 10 may analyze the results in combination. With this information, in addition to the Red, Yellow, and Green alerts, the system 10 may indicate possible causes for the results achieved. In SSEP Manual mode, signal response waveforms and amplitude and latency values associated with those waveforms are displayed for the user. The user then makes the comparison between a baseline the signal response.

The neuromonitoring system 10 may also conduct free-run EMG monitoring while the system is in any of the above-described modes. Free-run EMG monitoring continuously listens for spontaneous muscle activity that may be indicative of potential danger. The system 10 may automatically cycle into free-run monitoring after five seconds (by way of example only) of inactivity. Initiating a stimulation signal in the selected mode will interrupt the free-run monitoring until the system 10 has again been inactive for five seconds at which time the free-run begins again. FIG. 12 shows an exemplary screen view depicting free-run EMG monitoring from within the Nerve Retractor screen. Free-run monitoring is shown here in connection with the Nerve Retractor mode for exemplary purposes and it will be appreciated that Free-run EMG monitoring may be viewed in all modes.

To obtain $I_{thresh}$ and take advantage of the useful information it provides, the system 10 identifies and measures the peak-to-peak voltage ($V_{pp}$) of each EMG response corresponding to a given stimulation current ($I_{Stim}$). Identifying the true $V_{pp}$ of a response may be complicated by the existence of stimulation and/or noise artifacts which may create an erroneous $V_{pp}$ measurement. Noise, that is, electrical energy that is not part of the desired EMG signal may come from any number of potential sources (e.g. bovie equipment, other stimulators (such as external SSEP stimulators), wire disturbance, ambient noise, etc.) may be detected by the EMG sensors and comingled with the EMG signal. If the noise artifact occurs at an amplitude greater than or equal to the predetermined Vpp used to indicate a significant EMG response (e.g. 100 uV as described above) and when an evoked response is expected (i.e. within a T1, T2 window described below), or if it occurs during free run EMG, the result may be a false positive and unwarranted alarms may be triggered.

Figure 16:
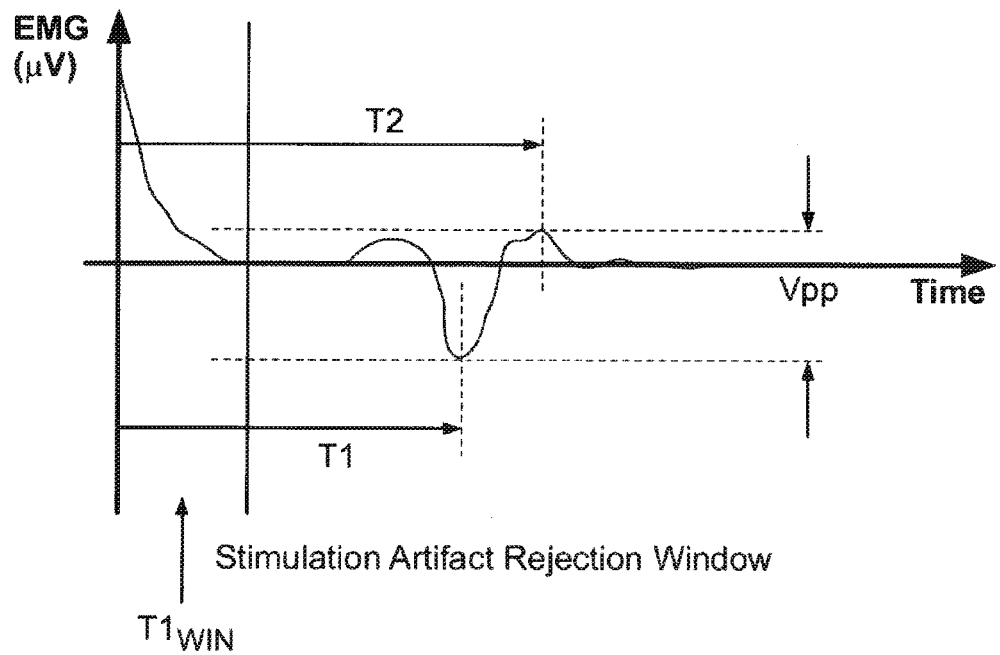
FIG. 16 is a graph illustrating a traditional stimulation artifact rejection technique as may be employed in obtaining each peak-to-peak voltage (Vpp) EMG response according to the present invention.
Figure 17:
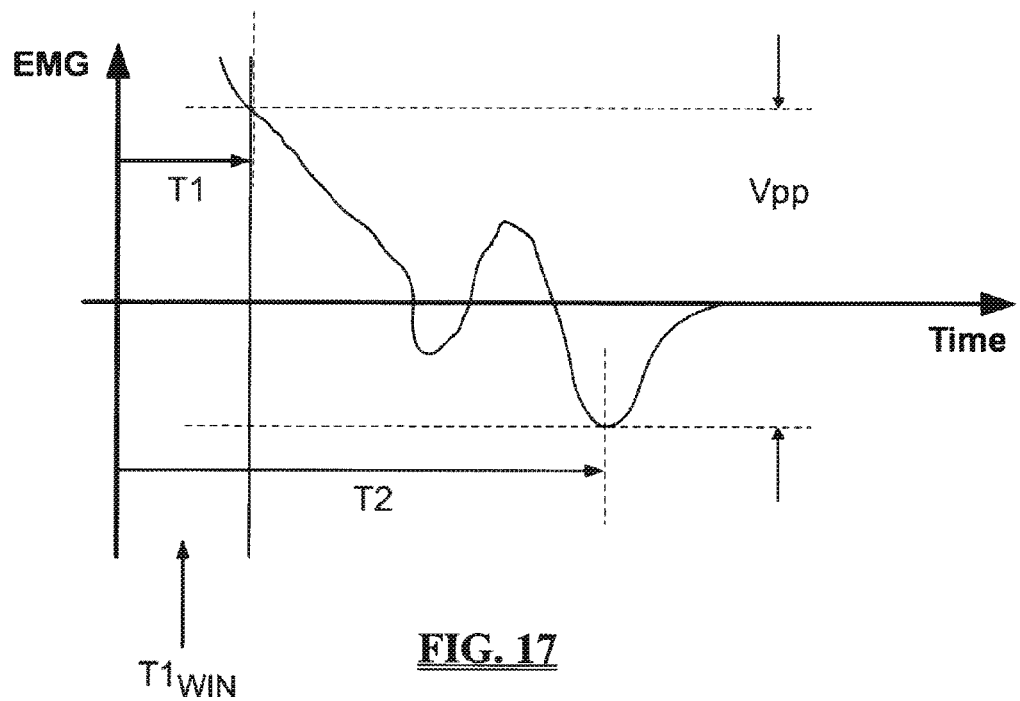
FIG. 17 is a graph illustrating the traditional stimulation artifact rejection technique of FIG. 16, wherein a large artifact rejection causes the EMG response to become compromised.

To overcome this challenge, the neuromonitoring system 10 of the present invention may employ any number of suitable artifact rejection techniques such as those shown and described in full in the above referenced co-pending and commonly assigned PCT App. Ser. No. PCT/US2004/025550, entitled "System and Methods for Performing Dynamic Pedicle Integrity Assessments," filed on Aug. 5, 2004. By way of example, the system 10 may utilize the traditional stimulation artifact rejection technique shown in FIG. 16. Under this technique, stimulation artifact rejection is undertaken by providing a simple artifact rejection window $T1_{WIN}$ at the beginning of the EMG waveform. During this T1 window, the EMG waveform is ignored and Vpp is calculated based on the max and min values outside this window. (T1 is the time of the first extremum (min or max) and T2 is the time of the second extremum.) In one embodiment, the artifact rejection window $T1_{WIN}$ may be set to about 7.3 msec. While generally suitable, there are situations where this stimulation artifact rejection technique of FIG. 16 is not optimum, such as in the presence of a large stimulation artifact (see FIG. 17). The presence of a large stimulation artifact causes the stimulation artifact to cross over the window $T1_{WIN}$ and blend in with the EMG. Making the stimulation artifact window larger is not effective, since there is no clear separation between EMG and stimulation artifact.

Figure 18:
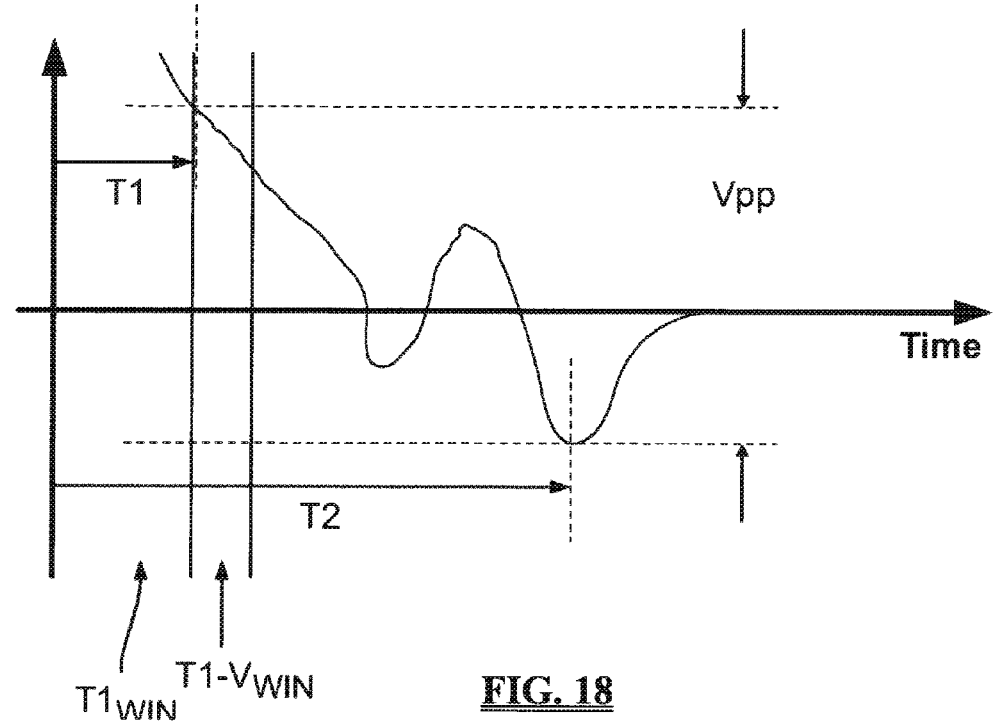
FIG. 18 is a graph illustrating an improved stimulation artifact rejection technique according to the present invention.

FIG. 18 illustrates a stimulation artifact rejection technique according to the present invention, which solves the above-identified problem with traditional stimulation artifact rejection. Under this technique, a T1 validation window (T1–$V_{WIN}$) is defined immediately following the T1 window ($T1_{WIN}$). If the determined Vpp exceeds the threshold for recruiting, but T1 falls within this T1 validation window, then the stimulation artifact is considered to be substantial and the EMG is considered to have not recruited. An operator may be alerted, based on the substantial nature of the stimulation artifact. This method of stimulation artifact rejection is thus able to identify situations where the stimulation artifact is large enough to cause the Vpp to exceed the recruit threshold. To account for noise, the T1 validation window (T1–$V_{WIN}$) should be within the range of 0.1 ms to 1 ms wide (preferably about 0.5 ms). The T1 validation window (T1–$V_{WIN}$) should not be so large that the T1 from an actual EMG waveform could fall within.

Figure 19:
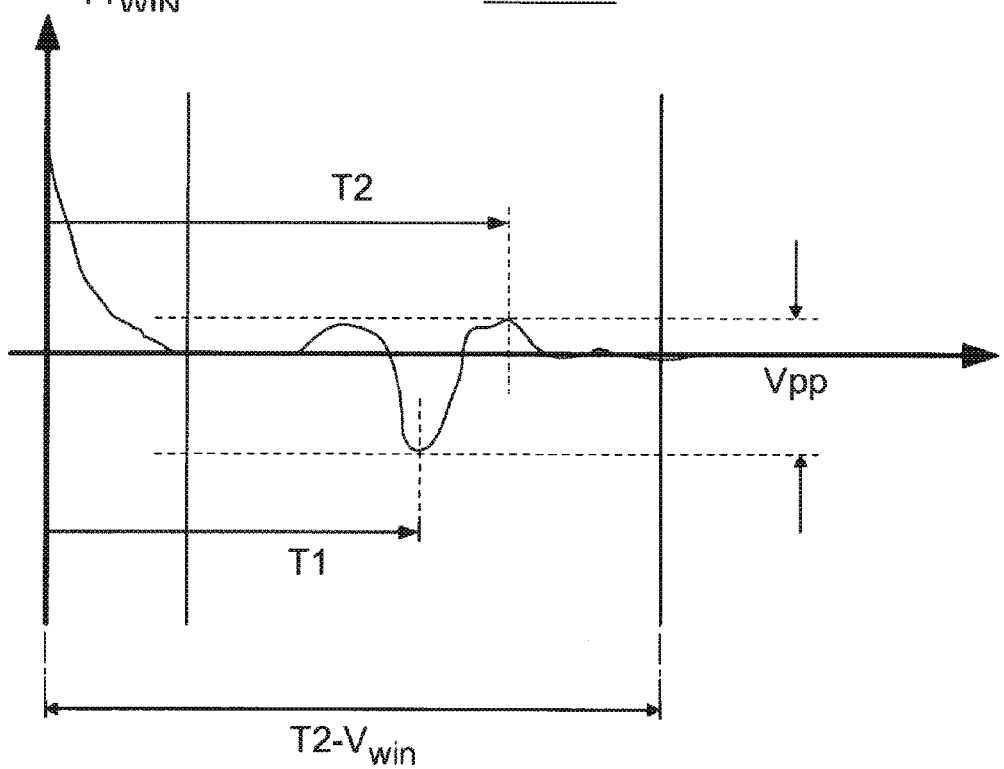
FIG. 19 is a graph illustrating an improved noise artifact rejection technique according to the present invention.

FIG. 19 illustrates a noise artifact rejection technique according to the present invention. When noise artifacts fall in the time window where an EMG response is expected, their presence can be difficult to identify. Artifacts outside the expected response window, however, are relatively easy to identify. The present invention capitalizes on this and defines a T2 validation window (T2–$V_{WIN}$) analogous to the T1 validation window (T1–$V_{WIN}$) described above with reference to FIG. 17. As shown, T2 must occur prior to a defined limit, which, according to one embodiment of the present invention, may be set having a range of between 40 ms to 50 ms (preferably about 47 ms). If the Vpp of the EMG response exceeds the threshold for recruiting, but T2 falls beyond the T2 validation window (T2–$V_{WIN}$), then the noise artifact is considered to be substantial and the EMG is considered to have not recruited. An operator may be alerted, based on the substantial nature of the noise artifact.

Figure 20:
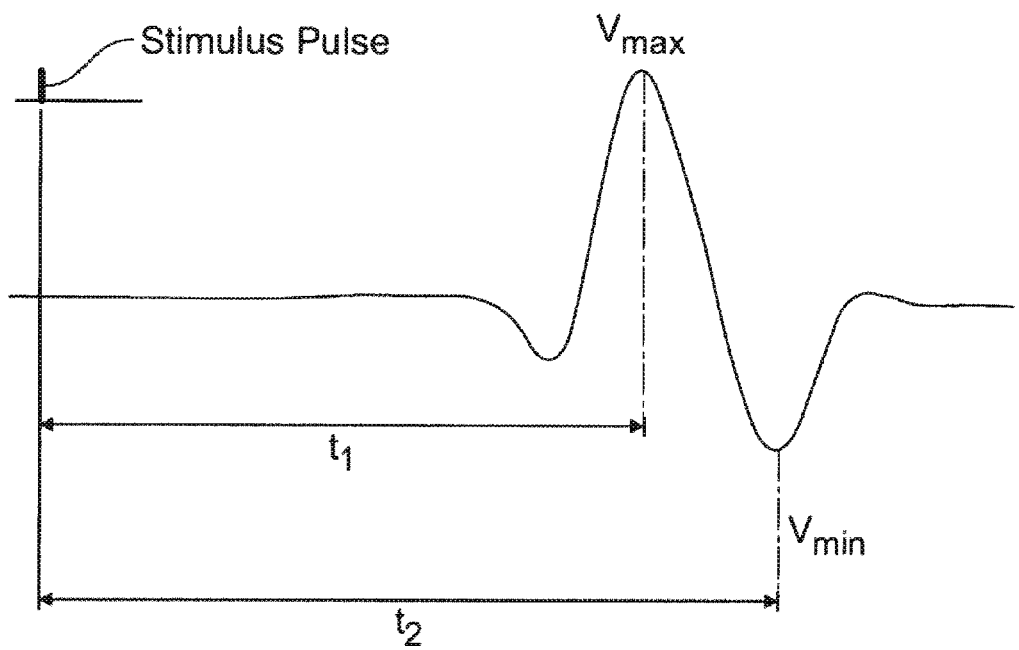
FIG. 20 is a graph illustrating a plot of a neuromuscular response (EMG) over time (in response to a stimulus current pulse) showing the manner in which voltage extrema ($V_{Max\ or\ Min}$), ($V_{Min\ or\ Max}$) occur at times T1 and T2, respectively.
Figure 21:
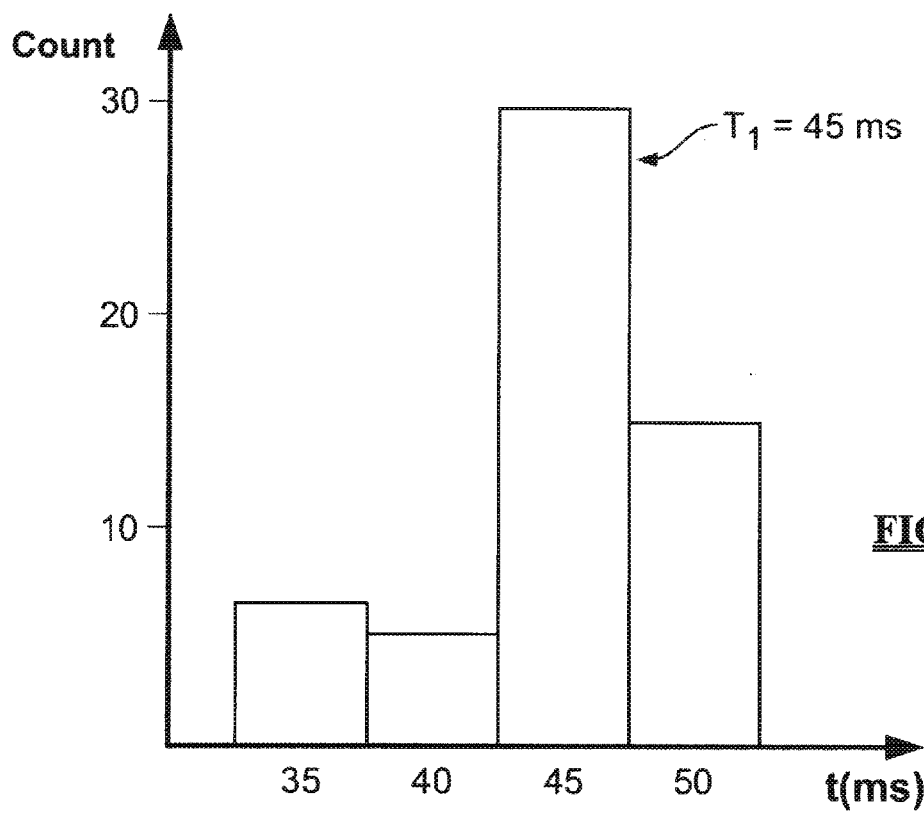
FIG. 21 is a graph illustrating a histogram as may be employed as part of a T1, T2 artifact rejection technique according to an alternate embodiment of the present invention.

FIG. 20 illustrates a still further manner of performing stimulation artifact rejection according to an alternate embodiment of the present invention. This artifact rejection is premised on the characteristic delay from the stimulation current pulse to the EMG response. For each stimulation current pulse, the time from the current pulse to the first extremum (max or min) is $T_1$ and to the second extremum (max or min) is $T_2$. As will be described below, the values of $T_1$, $T_2$ are each compiled into a histogram period (see FIG. 21). New values of $T_1$, $T_2$ are acquired for each stimulation and the histograms are continuously updated. The value of $T_1$ and $T_2$ used is the center value of the largest bin in the histogram. The values of $T_1$, $T_2$ are continuously updated as the histograms change. Initially Vpp is acquired using a window that contains the entire EMG response. After 20 samples, the use of $T_1$, $T_2$ windows is phased in over a period of 200 samples. $V_{max}$ and $V_{min}$ are then acquired only during windows centered around $T_1$, $T_2$ with widths of, by way of example only, 5 msec. This method of acquiring $V_{pp}$ automatically rejects the artifact if $T_1$ or $T_2$ fall outside of their respective windows.

According to another example, a technique distinguishing noise from a neurophysiologic event in order perform artifact rejection determines a signal-to-noise ration (SNR) of an EMG event. The SNR maybe very effective at indentifying a sinusoidal signals at any frequency and any amplitude. The SNR value is calculated by dividing the signal amplitude squared by the noise RMS value squared and converting to decibels. An ideal sine-wave will have an SNR of 3 dB, since by way of an example, a signal with an amplitude of 1.0 (S=1) will have an RMS of 0.707 (N=0.707). $10*\log 10(S^2/N^2) = 10*\log 10(1.0^2/0.707^2) = 10*\log 10(1.0/0.5) = 3.0$ dB.

Figure 22:
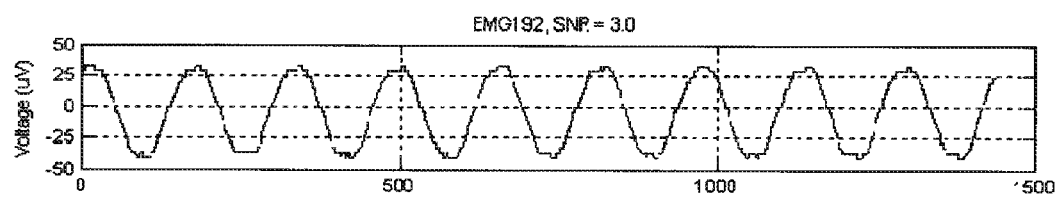
FIGS. 22-27 various plots of EMG data demonstrating how the system may distinguish noise signals from a neuromuscular response signal, according to one embodiment of the present invention, utilizing the a signal-to-noise ratio (SNR) of the signal.
Figure 23:
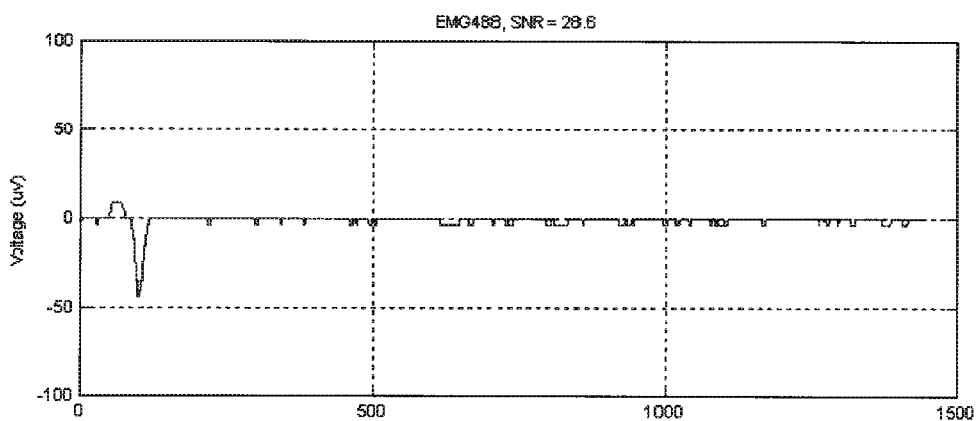
Figure 24:
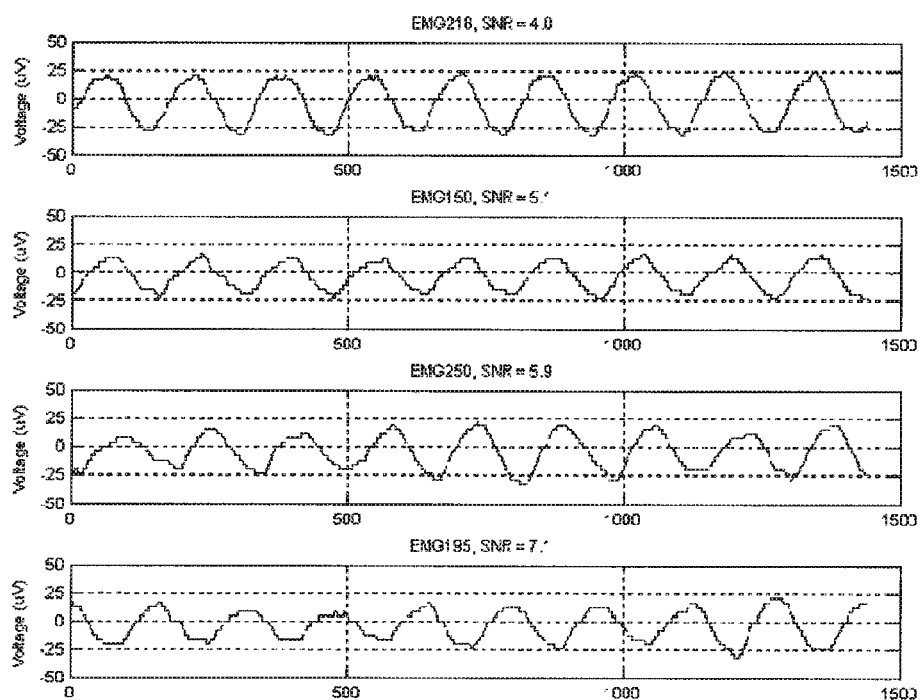
Figure 25:
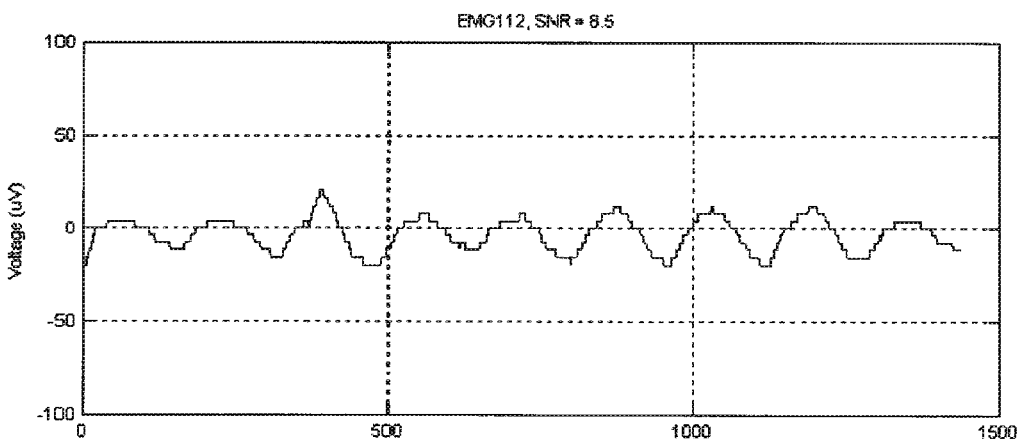
Figure 26:
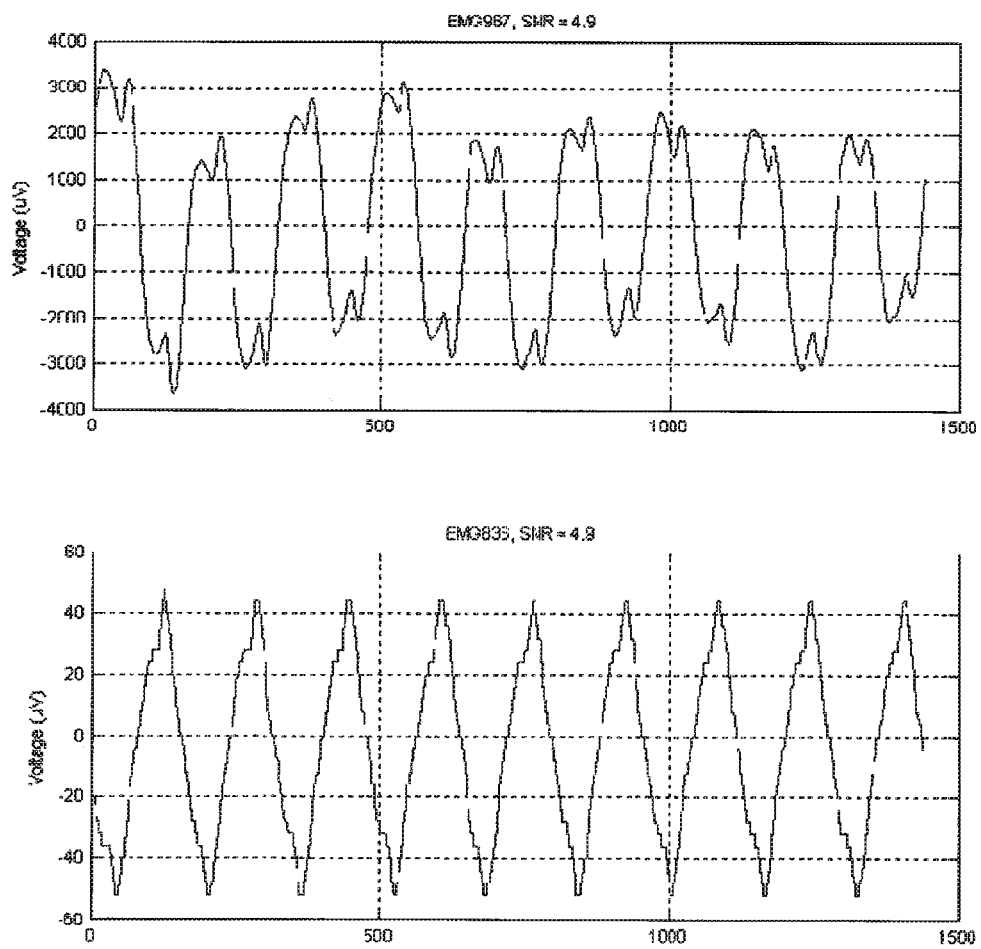
Figure 27:
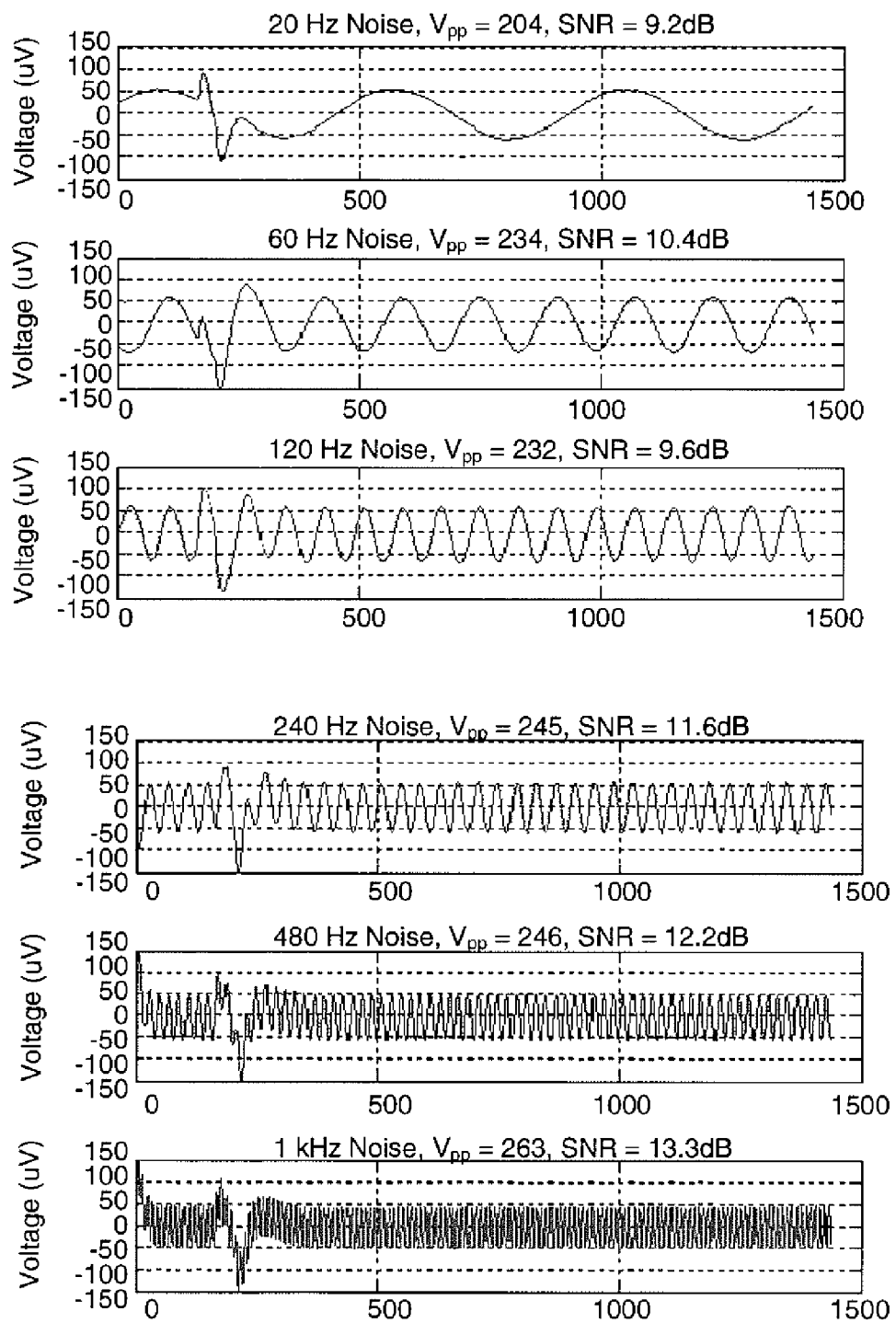

The SNR is very sensitive to any variation in the sine-wave so that virtually any noticeable perturbation will quickly drive the SNR value up. By way of example, FIG. 22 illustrates a noise signal with an SNR value of approximately 3 dB, while FIG. 23 illustrates a small neuromuscular response on a relatively clean (i.e. noiseless) channel having a large SNR of close to 30 dB. EMG signals with an SNR value below a predetermined value may be classified as noise by the system 10 and an alarm that would otherwise be initiated because the voltage exceeds the predetermined $V_{pp}$, may be bypassed. According to a preferred embodiment, the system 10 my classify the signal as noise if the SNR value is, by way of example only, 6.0 dB or below. FIG. 24 illustrates a series of EMG event plots having SNR values of 4, 5, and 6, respectively, and which may thus be ignored. FIG. 25, by contrast, illustrates an EMG event plot with a signal having an SNR of 8.5, which could, for example, represent a small neuromuscular response mixed with a 60 Hz signal. In addition to sine-waves, the SNR technique will reject a number of other signals that result in a low SNR, for example, triangular-waves and more complex signals comprised of 60 Hz+harmonics (FIG. 26). By way of example, FIG. 27 illustrates a series of EMG event plots showing 20, 60, 120, 240, 480, and 1000 Hz noise sources in which a neuromuscular response signal still has an SNR above 9 dB, such that the neuromuscular response would be noted but the remaining noise signals could be ignored (if for example, free run EMG was active).

According to another example, the system may utilize time-domain buffers to distinguish noise from a neurophysiologic event in order to perform artifact rejection. By way of example, the time-domain buffers may be particularly useful in processing free-run EMG events. This allows the sensitivity of the free-run to be customized based on frequency of events (in addition to amplitude). According to this example, each channel of system 10 is processed separately and a time-history buffer maintained for each one. The time history buffer stores event data (e.g. peak-to-peak, rms, SNR, etc). A short sliding window (of, for example, 1-3 seconds) may then be used to evaluate for the presence or absence of significant nerve activity within that window. The window duration could be fixed or adjustable by the user. Each individual event is qualified by the system 10 and then a "binary integrator" determines whether or not an alert should be initiated or not. By way of example, the binary integrator determines whether a predetermined minimum number of events occurred during a predetermined number of processing frames (seconds) and only when the number of events in the predetermined number of processing frames exceeds the predetermined value is an alert initiated.

Figure 28:
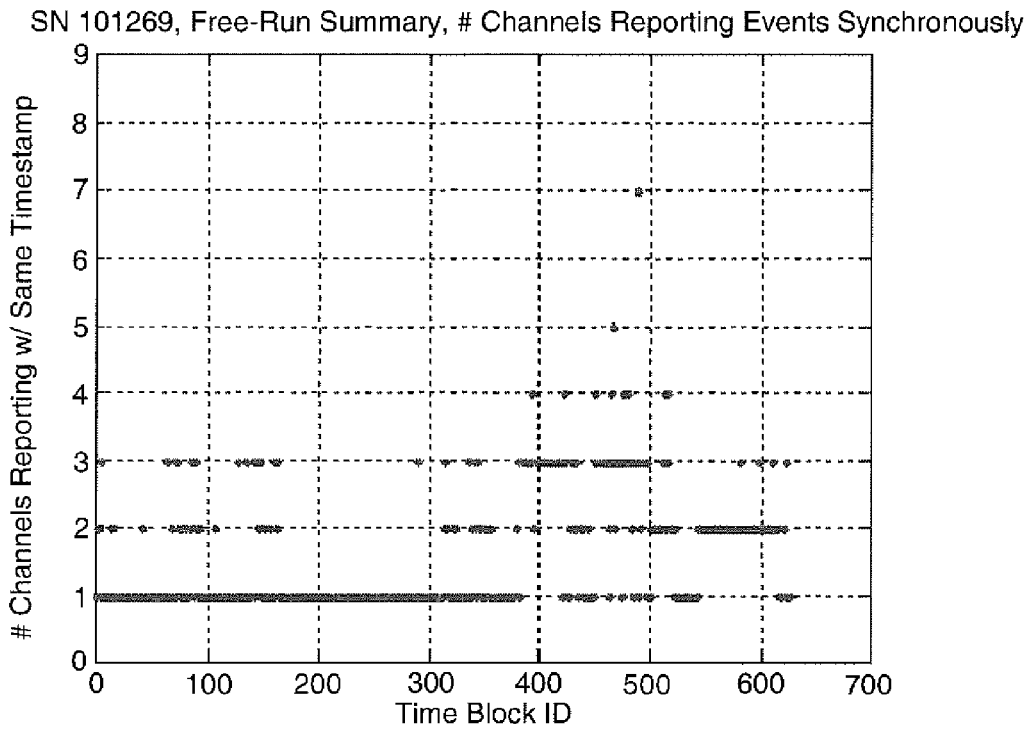
FIG. 28 is a graph of a time block window showing each EMG channel and illustrating the number of channels responding synchronously to an EMG event, according to another method utilized by the system to distinguish noise artifacts from neuromuscular responses.
Figure 29:
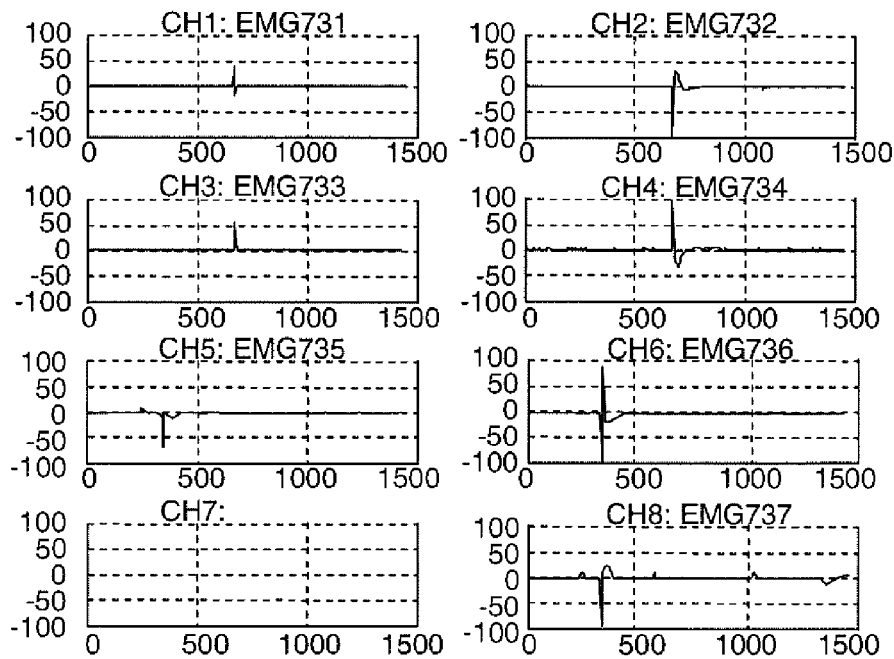
FIG. 29 illustrates a plot of each EMG waveform corresponding to the time block of FIG. 28.

According to still yet another example, the system may utilize multichannel snapshots to distinguish noise from a neurophysiologic event in order to perform artifact rejection. By way of example, the multi-channel snapshot may be particularly useful in processing free-run EMG events. According to this method, the system 10 assesses a "snapshot" of all channels at a single point in time. Certain noise, (e.g. bovie noise) may generate large responses synchronously on multiple channels, whereas neuromuscular responses are more likely to occur on a single channel or multiple channels with some spatial separation. Thus the system assesses the snapshot corresponding to an event and determines whether multiple channels are responding synchronously or not. The data may be used, for example, to reject and ignore an event as noise, or to alert the user to excessive interference during use. FIG. 28 is a graph illustrating this example. The x-axis is "time-block id" which shows each discrete event time. The y-axis shows the number of channels reporting events at each particular time block. Thus, in this example, at time block 300 there is only a single channel reporting an event. At time-block 488 on the other hand, there are 7 channels reporting events. If the system detects an event occurring at the same time block on multiple channels it may classify the signal as noise and bypass the alert. So for example, at time block 488 the system could attribute the responses to noise and not alert the user. To help illustrate, FIG. 29 depicts, by way of example, plots of EMG waveforms for each channel at time block 488 of FIG. 28.

In still another example, a technique for distinguishing noise from a neurophysiologic event in order perform artifact rejection determines a power-to-energy ratio an EMG event. The power-to-energy metric may be particularly useful in reducing false positives during free-run EMG when SSEP monitoring is being performed concurrently. The power-to-energy ratio is determined by dividing the largest single bin value by the total power in the signal. The metric is tunable so the threshold can be adjusted as desired to make it more or less sensitive. At the most sensitive setting, every point along the EMG signal is used in calculating the total power. To decrease the sensitivity, the number of points used may be decreased. When the power/energy ratio exceeds a predetermined value, the signal may be classified as noise and ignored. Typical biologic waveforms will have a metric well below 0.10, with a very clean tri-phasic waveform having a metric of 0.02ish, and the metric will drop from that level as more noise is added to the waveform.

Figure 30:
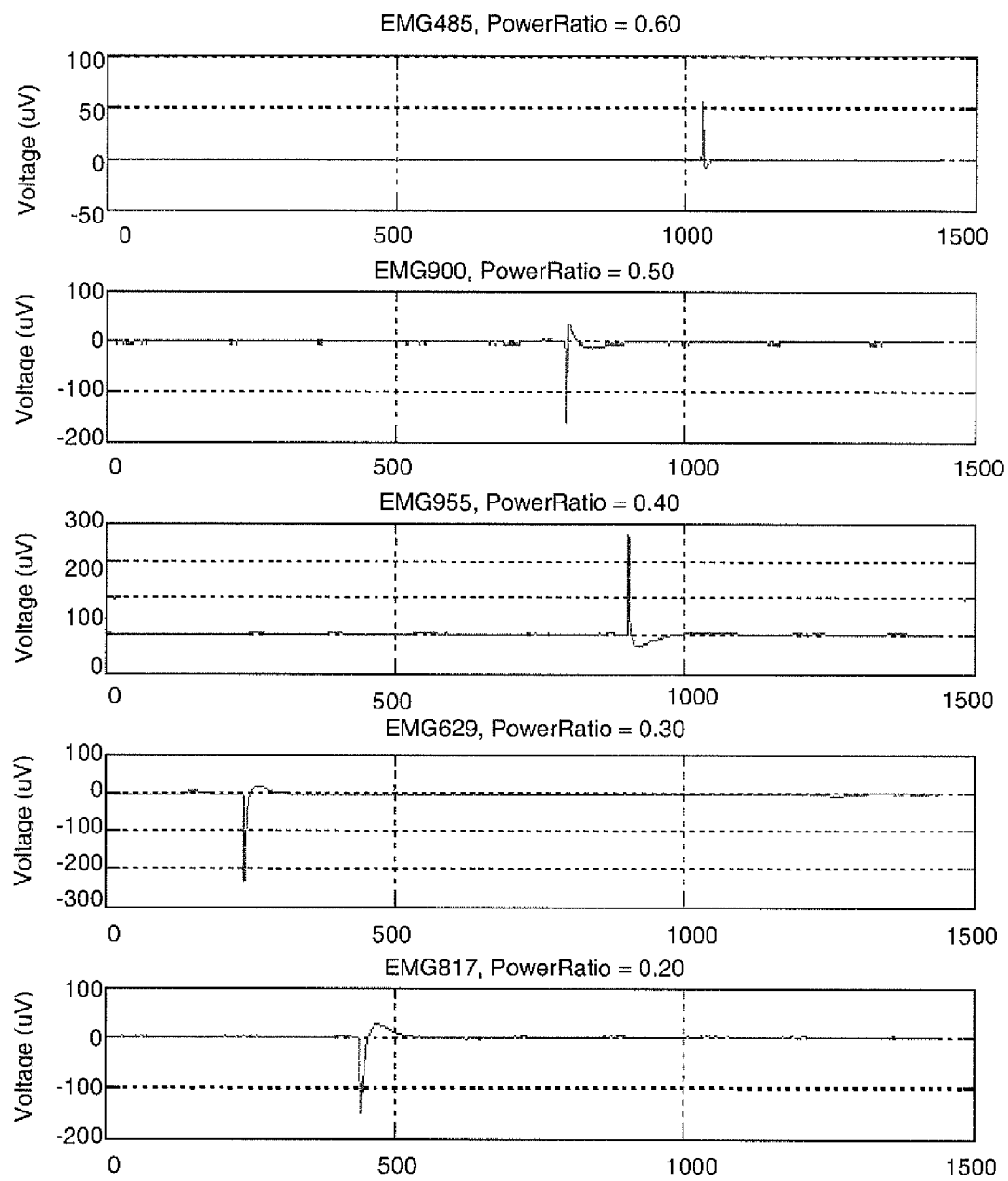
FIG. 30 illustrates a series of plots having a power to energy metric at or above a threshold indicating likely SSEP events, according to one example method of distinguishing neuromuscular responses from SSEP events.
Figure 31:
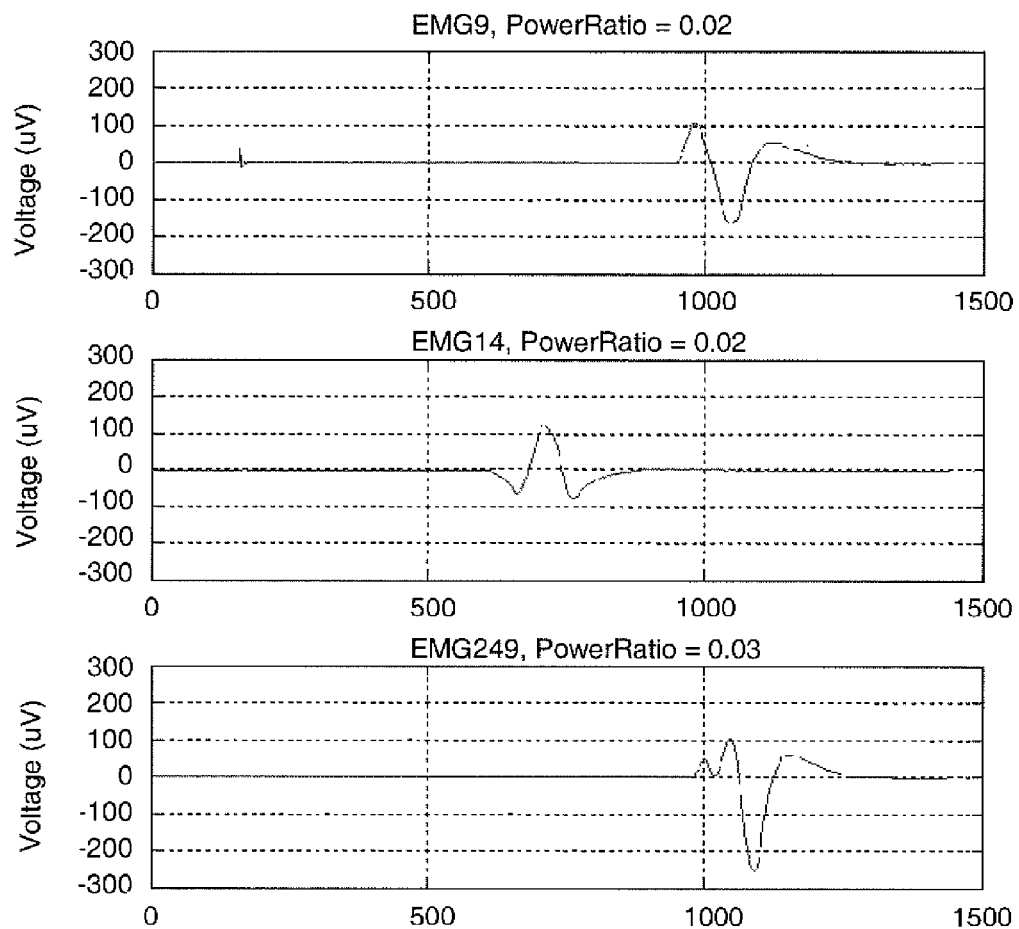
FIG. 31 illustrates a series of plots having a power to energy metric below the a threshold indicating likely SSEP events, according to one example method of distinguishing neuromuscular responses from SSEP events; that embodiment the SNR ratio is used to determine what is and what is not a noise artifact.

By way of example, according to a preferred embodiment, when the power-to-energy ratio reaches or exceeds 0.20 (which means the single largest bin is contributing 20% of the total power), the signal may be classified as noise and ignored. When the power-to-energy ratio is above 0.20 the likelihood that the event represents a true neuromuscular response is marginal. Additionally, the system may combine the metric with other data to determine whether the event occurred on multiple channels (e.g. since SSEP events typically appear on multiple channels) to ignore these events in free run and reduce false positives. FIG. 30 illustrates, by way of example only, a series of plots having the power-to-energy ratio at or above the 0.20 threshold, indicating likely SSEP events. FIG. 31 illustrates, by way of example only, a series of plots having three typical biologic free-run events with their corresponding metric of around 0.02.

According to still another technique for distinguishing noise from a neurophysiologic event in order perform artifact rejection, the system may again determine a power-to-energy ratio and then extract the responsible portion of the signal if the power-to-noise ration exceeds a predetermined value. This method may, for example only, be particularly useful in detecting and removing SSEP spikes from EMG waveforms. SSEP spikes are generally transient in nature, typically lasting around 10-20 time-samples. Thus the system 10 determines the power-to energy ration, again by dividing the largest single bin value by the total power in the signal.

The algorithm functions as follows:
1) Identify an SSEP Spike by looking at the Power Ratio formed by dividing the single largest bin value by the total power in the signal. If the Power Ratio is above 0.2, then SSEP spike is likely. According to one example, the waveform may be broken up into a "front" and "back" half since there are a fair number of waveforms that have a "primary" SSEP in the first half of the recorded waveform, and a "secondary" SSEP spike in the second half.
2) Zoom in around the potential SSEP Spike and extract the (time-sample) indices and voltage levels for the min and max values.
3) Take the indices and expand them by +−5 time samples, to completely capture the SSEP Spike in its own window.
4) Replace these window values with the linearly-interpolated values of the 2 data points adjacent to the window.

FIGS. 32-36 illustrate a series of plots showing the EMG data before and after filtering for SSEP spikes. In each, the heavier line 302 represents the EMG data after removal of the SSEP spike, and the thinner line 301 represents the EMG data with the SSEP spikes. The upper subplots show raw data, and the lower subplots show low-pass (biquad) filtered data.

Figure 32:
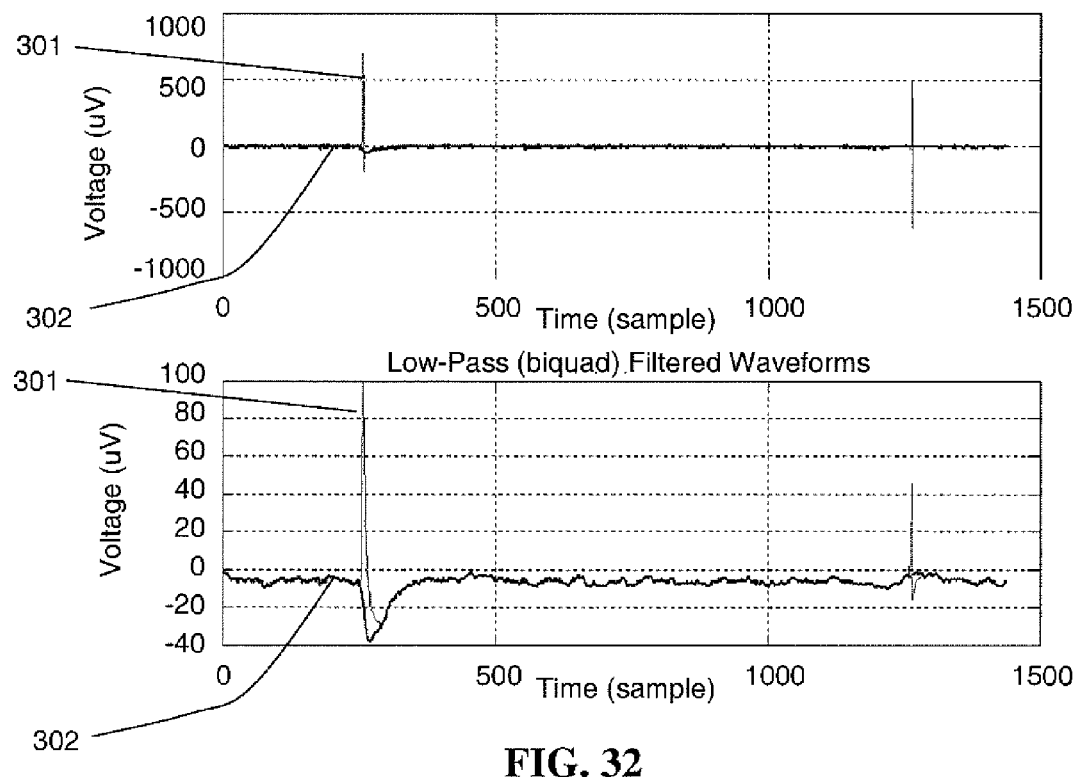
FIGS. 32-36 illustrate a series of plots showing EMG data before and after filtering for SSEP spikes according to another example embodiment of a method for rejecting noise artifacts.
Figure 33:
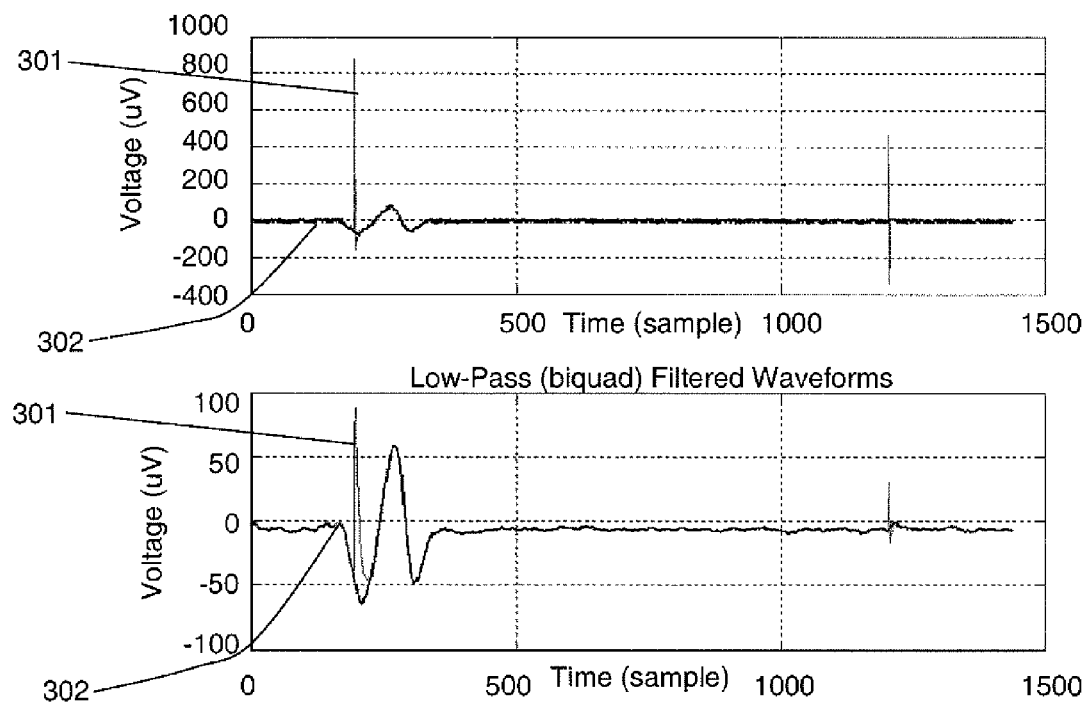
Figure 34:
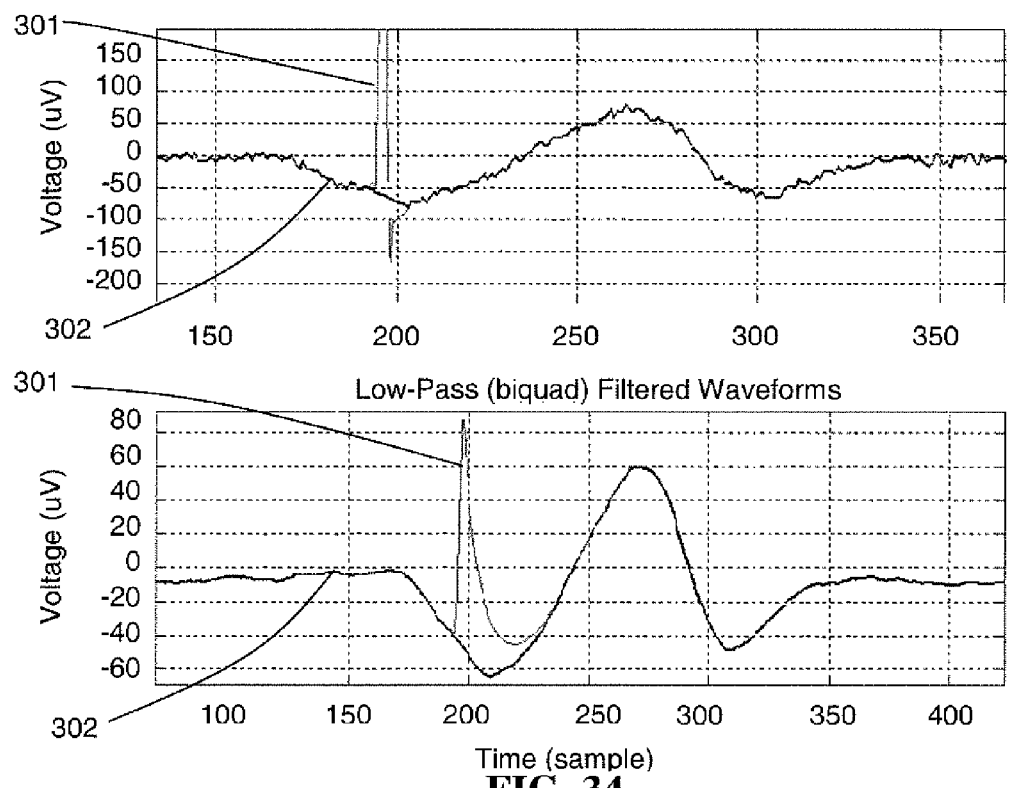
Figure 35:
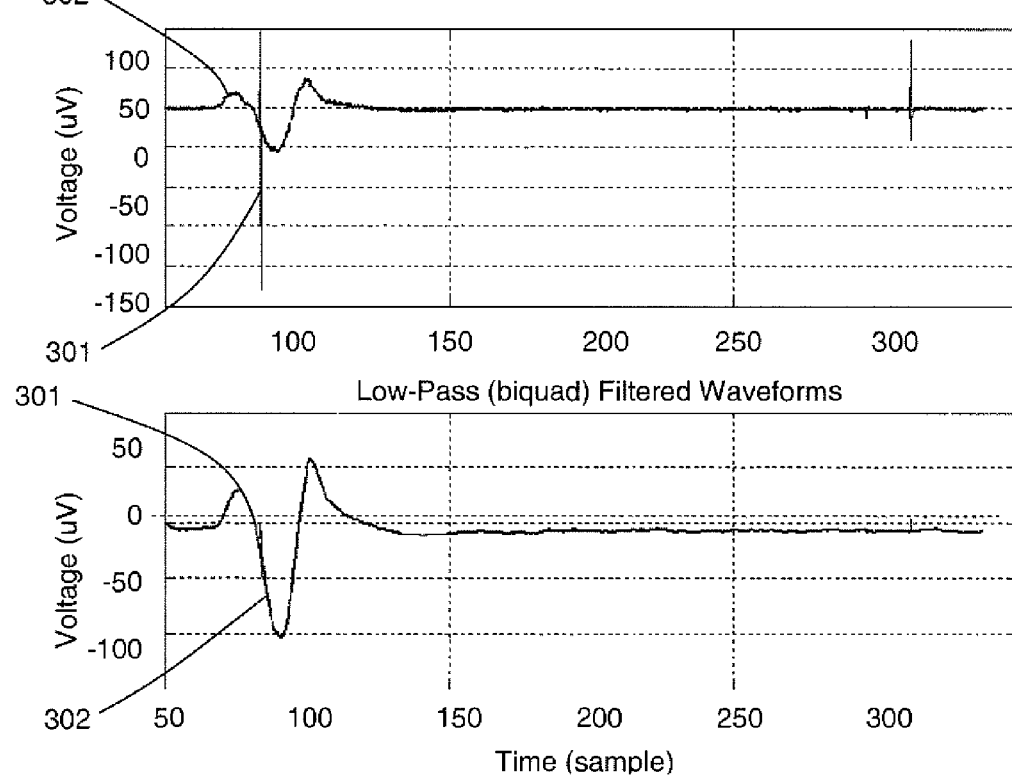
Figure 36:
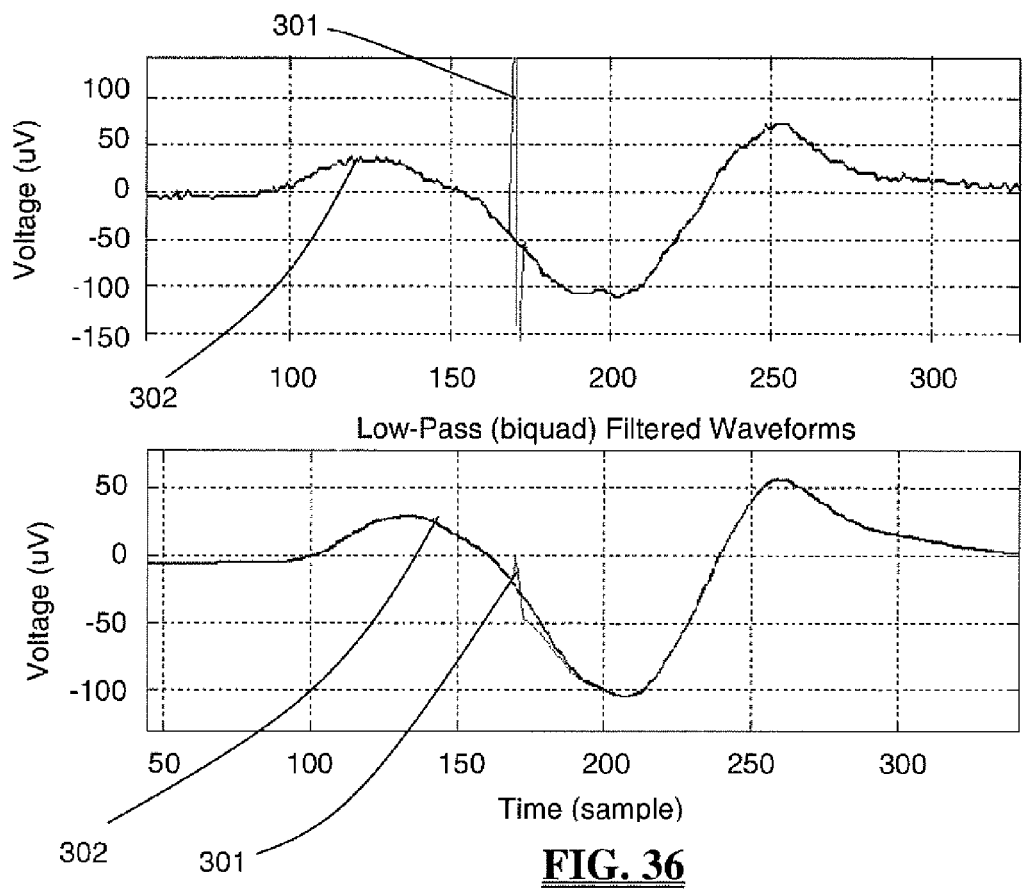

FIG. 32 illustrates two SSEP spikes captured in an EMG waveform, during Nerve Detection. The large initial spike would trigger a false positive during the procedure, since after low-pass filtering the resulting spike still has a peak-to-peak (Vpp) value above 100 uV (by way of example). The initial spike has a very large initial value, then a much smaller overshoot with an extended tail. As can be seen, in line 302 both of the SSEP spikes have been removed by the SSEP filter. The tail of the first spike is still present but the Vpp value is now approximately 40 uV and does not trigger an event. FIG. 33 shows a similar plot to that of FIG. 32 except that the SSEP spike occurs at the same time as a neuromuscular response. As illustrated by line 302, removing the SSEP spike with the SSEP filter has very little effect on the underlying waveform corresponding to the neuromuscular response. FIG. 34 is a zoomed in view of the plot of FIG. 33. FIG. 35 is another example of an SSEP spike occurring during a neuromuscular response. Again, using the SSEP filter has very little effect on the underlying neuromuscular response waveform. FIG. 36 is a zoomed in view of the plot of FIG. 35.

Upon measuring $V_{pp}$ for each EMG response, the $V_{pp}$ information is analyzed relative to the corresponding stimulation current ($I_{stim}$) in order to identify the minimum stimulation current ($I_{thresh}$) capable of resulting in a predetermined $V_{pp}$ EMG response. According to the present invention, the determination of $I_{thresh}$ may be accomplished via any of a variety of suitable algorithms or techniques.

FIGS. 37A-37D illustrates, by way of example only, the principles of a threshold hunting algorithm of the present invention used to quickly find $I_{thresh}$. The method for finding $I_{thresh}$ utilizes a bracketing method and a bisection method. The bracketing method quickly finds a range (bracket) of stimulation currents that must contain $I_{thresh}$ and the bisection method narrows the bracket until $I_{thresh}$ is known within a specified accuracy. If the stimulation current threshold, $I_{thresh}$, of a channel exceeds a maximum stimulation current, that threshold is considered out of range.

Figure 37A:
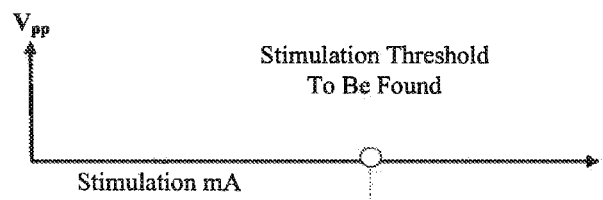
FIGS. 37A-37D are graphs illustrating the fundamental steps of a rapid current threshold-hunting algorithm according to one embodiment of the present invention.
Figure 37B:
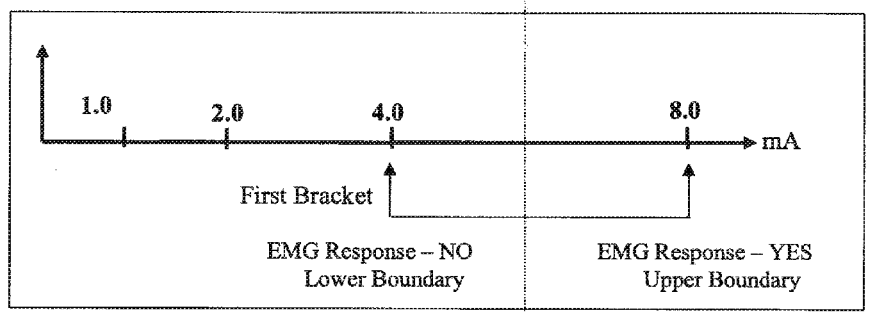

FIG. 37B illustrates the bracketing feature of the threshold hunting algorithm of the present invention. Stimulation begins at a minimum stimulation current, such as (by way of example only) 1 mA. It will be appreciated that the relevant current values depend in part on the function performed (e.g. high currents are used for MEP and low currents are generally used for other functions) and the values current values described here are for purposes of example only and may in actuality be adjusted to any scale The level of each subsequent stimulation is doubled from the preceding stimulation level until a stimulation current recruits (i.e. results in an EMG response with a $V_{pp}$ greater or equal to $V_{thresh}$). The first stimulation current to recruit (8 mA in FIG. 37B), together with the last stimulation current to have not recruited (4 mA in FIG. 7B), forms the initial bracket.

Figure 37C:
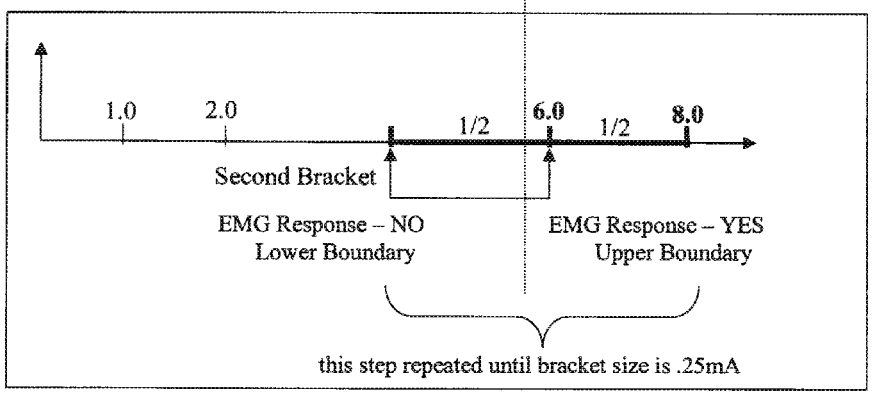
Figure 37D:
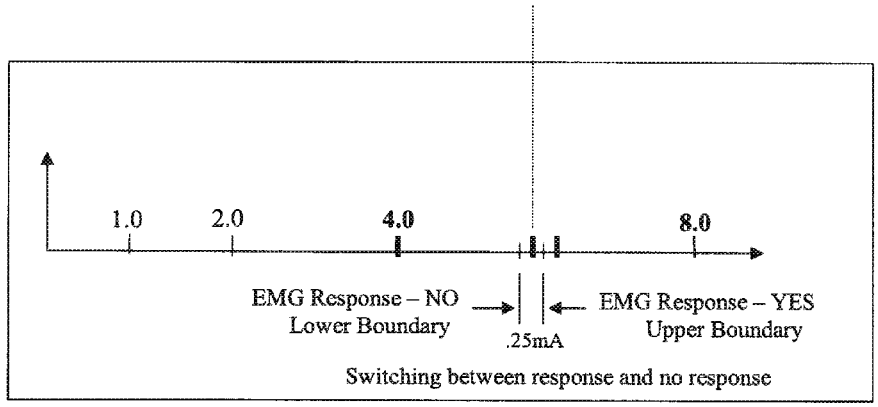

FIGS. 37C-37D illustrate the bisection feature of the threshold hunting algorithm of the present invention. After the threshold current $I_{thresh}$ has been bracketed (FIG. 37B), the initial bracket is successively reduced via bisection to a predetermined width, such as (by way of example only) 0.25 mA. This is accomplished by applying a first bisection stimulation current that bisects (i.e. forms the midpoint of) the initial bracket (6 mA in FIG. 37C). If this first bisection stimulation current recruits, the bracket is reduced to the lower half of the initial bracket (e.g. 4 mA and 6 mA in FIG. 37C). If this first bisection stimulation current does not recruit, the bracket is reduced to the upper half of the initial bracket (e.g. 6 mA and 8 mA in FIG. 37C). This process is continued for each successive bracket until $I_{thresh}$ is bracketed by this stimulation currents separated by the predetermined width (which, in case, is 0.25 mA). In this example shown, this would be accomplished by applying a second bisection stimulation current (forming the midpoint of the second bracket, or 5 mA in this example). Because this second bisection stimulation current is below $I_{thresh}$, it will not recruit. As such, the second bracket will be reduced to the upper half thereof (5 mA to 6 mA), forming a third bracket. A third bisection stimulation current forming the mid-point of the third bracket (5.50 mA in this case) will then be applied. Because this third bisection stimulation current is below $I_{thresh}$, it will not recruit. As such, the third bracket will be reduced to the upper half thereof (5.50 mA to 6 mA), forming a fourth bracket. A fourth bisection stimulation current forming the mid-point of the fourth bracket (5.75 mA in this case) will then be applied. Because the fourth bisection stimulation current is above $I_{thresh}$, it will recruit. The final bracket is therefore between 5.50 mA and 5.75 mA. Due to the "response" or recruitment at 5.50 mA and "no response" or lack of recruitment at 5.75 mA, it can be inferred that $I_{thresh}$ within this range. In one embodiment, the midpoint of this final bracket may be defined as $I_{thresh}$, any value falling within the final bracket may be selected as $I_{thresh}$ without departing from the scope of the present invention. Depending on the active mode, the algorithm may stop after finding $I_{thresh}$ for the first responding channel (i.e. the channel with the lowest $I_{thresh}$) or the bracketing and bisection steps may be repeated for each channel to determine $I_{thresh}$ for each channel. Additionally, in the "dynamic" functional modes, including, but not necessarily limited to Dynamic Screw Test and MaXcess Detection, the system may continuously update the stimulation threshold level and indicate that level to the user. To do so, the threshold hunting algorithm does not repeatedly determine the $I_{thresh}$ level anew, but rather, it determines whether stimulation current thresholds are changing. This is accomplished, as illustrated in FIG. 37D, by a monitoring phase that involves switching between stimulations at lower and upper ends of the final bracket. If the threshold has not changed then the lower stimulation current should not evoke a response, while the upper end of the bracket should. If either of these conditions fail, the bracket is adjusted accordingly. The process is repeated for each of the active channels to continue to assure that each threshold is bracketed. If stimulations fail to evoke the expected response three times in a row, then the algorithm transitions back to the bracketing state in order to reestablish the bracket.

For some functions, such as (by way of example) MEP and Nerve Retractor modes, it may be desirable to obtain $I_{thresh}$ for each active channel each time the function is performed. This is particularly advantageous when assessing changes in $I_{thresh}$ over time as a means to detect potential problems (as opposed to detecting an $I_{thresh}$ below a predetermined level determined to be safe, such as in the Screw Test modes). While $I_{thresh}$ can be found for each active channel using the algorithm as described above, it requires a potentially large number of stimulations, each of which is associated with a specific time delay, which can add significantly to the response time. Done repeatedly, it could also add significantly to the overall time required to complete the surgical procedure, which may present added risk to the patient and added costs. To overcome this drawback, a preferred embodiment of the neuromonitoring system 10 boasts a multi-channel threshold hunting algorithm so as to quickly determine $I_{thresh}$ for each channel while minimizing the number of stimulations and thus reduce the time required to perform such determinations.

The multi-channel threshold hunting algorithm reduces the number stimulations required to complete the bracketing and bisection steps when $I_{thresh}$ is being found for multiple channels. The multi-channel algorithm does so by omitting stimulations for which the result is predictable from the data already acquired. When a stimulation signal is omitted, the algorithm proceeds as if the stimulation had taken place. However, instead of reporting an actual recruitment result, the reported result is inferred from previous data. This permits the algorithm to proceed to the next step immediately, without the time delay associated with a stimulation signal.

Regardless of what channel is being processed for $I_{thresh}$, each stimulation signal elicits a response from all active channels. That is to say, every channel either recruits or does not recruit in response to a stimulation signal (again, a channel is said to have recruited if a stimulation signal evokes an EMG response deemed to be significant on that channel, such as $V_{pp}$ of approximately 100 uV). These recruitment results are recorded and saved for each channel. Later, when a different channel is processed for $I_{thresh}$, the saved data can be accessed and, based on that data, the algorithm may omit a stimulation signal and infer whether or not the channel would recruit at the given stimulation current.

There are two reasons the algorithm may omit a stimulation signal and report previous recruitment results. A stimulation signal may be omitted if the selected stimulation current would be a repeat of a previous stimulation. By way of example only, if a stimulation current of 1 mA was applied to determine $I_{thresh}$ for one channel, and a stimulation at 1 mA is later required to determine $I_{thresh}$ for another channel, the algorithm may omit the stimulation and report the previous results. If the specific stimulation current required has not previously been used, a stimulation signal may still be omitted if the results are already clear from the previous data. By way of example only, if a stimulation current of 2 mA was applied to determine $I_{thresh}$ for a previous channel and the present channel did not recruit, when a stimulation at 1 mA is later required to determine $I_{thresh}$ for the present channel, the algorithm may infer from the previous stimulation that the present channel will not recruit at 1 mA because it did not recruit at 2 mA. The algorithm may therefore omit the stimulation and report the previous result.

Figure 38:
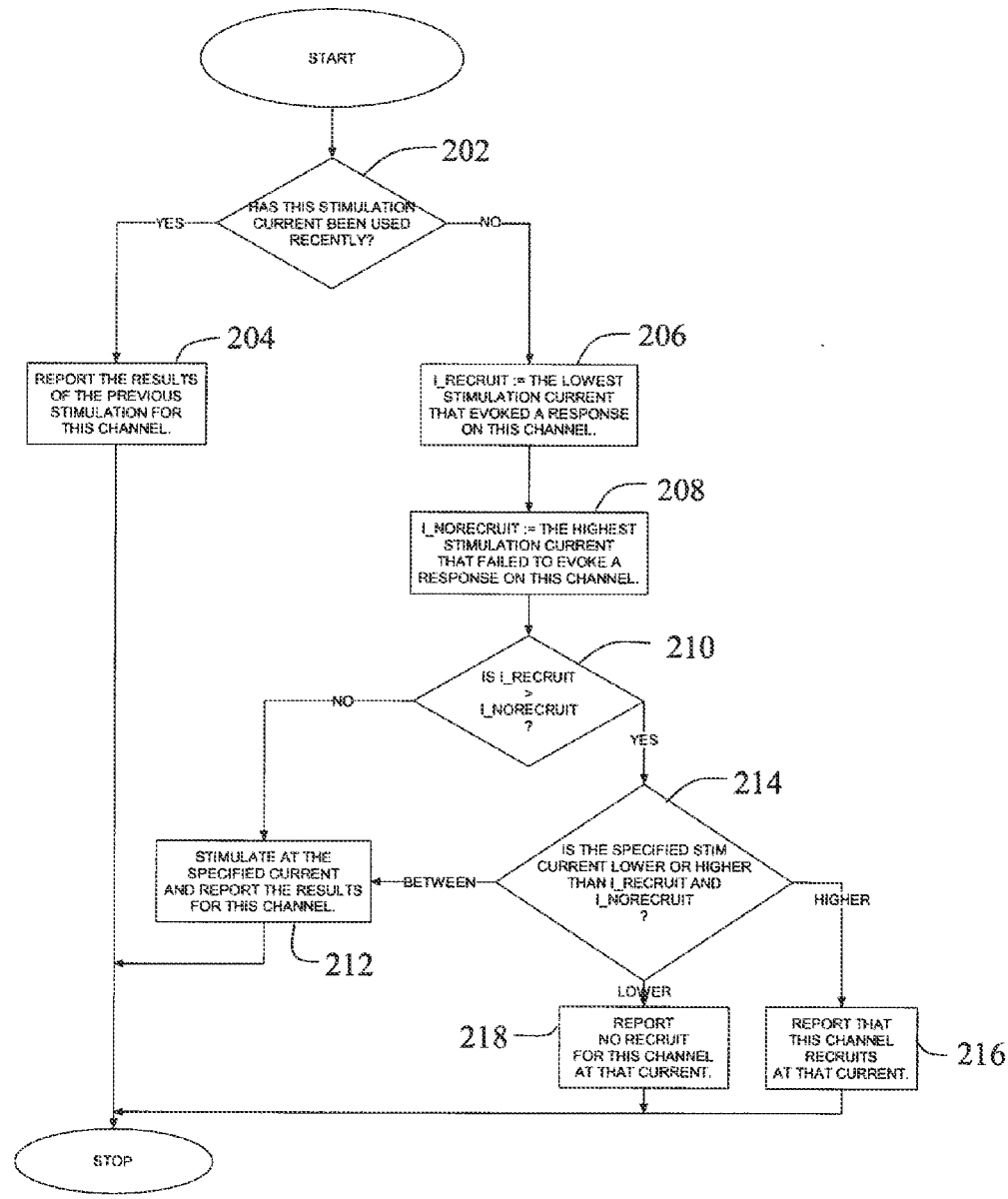
FIG. 38 is a flowchart illustrating the method by which a multi-channel hunting algorithm determines whether to perform or omit a stimulation.

FIG. 38 illustrates (in flowchart form) a method by which the multi-channel threshold hunting algorithm determines whether to stimulate, or not stimulate and simply report previous results. The algorithm first determines if the selected stimulation current has already been used (step 202). If the stimulation current has been used, the stimulation is omitted and the results of the previous stimulation are reported for the present channel (step 204). If the stimulation current has not been used, the algorithm determines $L_{recruit}$ (step 206) and $I_{recruit}$ (step 208) for the present channel. $I_{recruit}$ is the lowest stimulation current that has recruited on the present channel. $I_{nonrecruit}$ is the highest stimulation current that has failed to recruit on the present channel. The algorithm next determines whether $I_{recruit}$ is greater than $I_{nonrecruit}$ (step 210). An $L_{recruit}$ that is not greater than $I_{nonrecruit}$ is an indication that changes have occurred to $I_{thresh}$ on that channel. Thus, previous results may not be reflective of the present threshold state and the algorithm will not use them to infer the response to a given stimulation current. The algorithm will stimulate at the selected current and report the results for the present channel (step 212). If $I_{recruit}$ is greater than $I_{nonrecruit}$, the algorithm determines whether the selected stimulation current is higher than $L_{recruit}$, lower than $I_{nonrecruit}$, or between $I_{recruit}$ and $I_{nonrecruit}$ (step 214). If the selected stimulation current is higher than $L_{recruit}$, the algorithm omits the stimulation and reports that the present channel recruits at the specified current (step 216). If the selected stimulation current is lower than $I_{nonrecruit}$, the algorithm infers that the present channel will not recruit at the selected current and reports that result (step 218). If the selected stimulation current falls between $I_{recruit}$ and $I_{nonrecruit}$, the result of the stimulation cannot be inferred and the algorithm stimulates at the selected current and reports the results for the present channel (step 212). This method may be repeated until $I_{thresh}$ has been determined for every active channel.

In the interest of clarity, FIGS. 39A-39C demonstrate use of the multi-channel threshold hunting algorithm to determine $I_{thresh}$ on only two channels. It should be appreciated, however, that the multi-channel algorithm is not limited to finding $I_{thresh}$ for two channels, but rather it may be used to find $I_{thresh}$ for any number of channels, such as (for example) eight channels according to a preferred embodiment of the neuromonitoring system 10. With reference to FIG. 39A, channel 1 has an $I_{thresh}$ to be found of 6.25 mA and channel 2 has an $I_{thresh}$ to be found of 4.25 mA. $I_{thresh}$ for channel 1 is found first as illustrated in FIG. 39B, using the bracketing and bisection methods discussed above. Bracketing begins at the minimum stimulation current (for the purposes of example only) of 1 mA. As this is the first channel processed and no previous recruitment results exist, no stimulations are omitted. The stimulation current is doubled with each successive stimulation until a significant EMG response is evoked at 8 mA. The initial bracket of 4 mA-8 mA is bisected, using the bisection method described above, until the stimulation threshold, $I_{thresh}$, is contained within a final bracket separated by the selected width or resolution (again 0.25 mA). In this example, the final bracket is 6 mA-6.25 mA. $I_{thresh}$ may be defined as any point within the final bracket or as the midpoint of the final bracket (6.125 mA in this case). In either event, $I_{thresh}$ is selected and reported as $I_{thresh}$ for channel 1.

Once $I_{thresh}$ is found for channel 1, the algorithm turns to channel 2, as illustrated in FIG. 39C. The algorithm begins to process channel 2 by determining the initial bracket, which is again 4 mA-8 mA. All the stimulation currents required in the bracketing state were used in determining $I_{thresh}$ for channel 1. The algorithm refers back to the saved data to determine how channel 1 responded to the previous stimulations. From the saved data, the algorithm may infer that channel 2 will not recruit at stimulation currents of 1, 2, and 4 mA, and will recruit at 8 mA. These stimulations are omitted and the inferred results are displayed. The first bisection stimulation current selected in the bisection process (6 mA in this case), was previously used and, as such, the algorithm may omit the stimulation and report that channel 2 recruits at that stimulation current. The next bisection stimulation current selected (5 mA in this case) has not been previously used and, as such, the algorithm must determine whether the result of a stimulation at 5 mA may still be inferred. In the example shown, $I_{recruit}$ and $I_{nonrecruit}$ are determined to be 6 mA and 4 mA, respectively. Because 5 mA falls in between $I_{recruit}$ and $I_{nonrecruit}$, the algorithm may not infer the result from the previous data and, as such, the stimulation may not be omitted. The algorithm then stimulates at 5 mA and reports that the channel recruits. The bracket is reduced to the lower half (making 4.50 mA the next bisection stimulation current). A stimulation current of 4.5 mA has not previously been used and, as such, the algorithm again determines $I_{recruit}$ and $I_{nonrecruit}$ (5 mA and 4 mA in this case). The selected stimulation current (4.5 mA) falls in between $I_{recruit}$ an $I_{nonrecruit}$ and, as such, the algorithm stimulates at 4.5 mA and reports the results. The bracket now stands at its final width of 0.25 mA (for the purposes of example only). $I_{thresh}$ may be defined as any point within the final bracket or as the midpoint of the final bracket (4.125 mA in this case). In either event, $I_{thresh}$ is selected and reported as $I_{thresh}$ for channel 2.

Although the multi-channel threshold hunting algorithm is described above processing channels in numerical order, it will be understood that the actual order in which channels are processed is immaterial. The channel processing order may be biased to yield the highest or lowest threshold first (discussed below) or an arbitrary processing order may be used. Furthermore, it will be understood that it is not necessary to complete the algorithm for one channel before beginning to process the next channel, provided that the intermediate state of the algorithm is retained for each channel. Channels are still processed one at a time. However, the algorithm may cycle between one or more channels, processing as few as one stimulation current for that channel before moving on to the next channel. By way of example only, the algorithm may stimulate at 10 mA while processing a first channel for $I_{thresh}$. Before stimulating at 20 mA (the next stimulation current in the bracketing phase), the algorithm may cycle to any other channel and process it for the 10 mA stimulation current (omitting the stimulation if applicable). Any or all of the channels may be processed this way before returning to the first channel to apply the next stimulation Likewise, the algorithm need not return to the first channel to stimulate at 20 mA, but instead may select a different channel to process first at the mA level. In this manner, the algorithm may advance all channels essentially together and bias the order to find the lower threshold channels first or the higher threshold channels first. By way of example only, the algorithm may stimulate at one current level and process each channel in turn at that level before advancing to the next stimulation current level. The algorithm may continue in this pattern until the channel with the lowest $I_{thresh}$ is bracketed. The algorithm may then process that channel exclusively until $I_{thresh}$ is determined, and then return to processing the other channels one stimulation current level at a time until the channel with the next lowest $I_{thresh}$ is bracketed. This process may be repeated until $I_{thresh}$ determined for each channel in order of lowest to highest $I_{thresh}$. If $I_{thresh}$ for more than one channel falls within the same bracket, the bracket may be bisected, processing each channel within that bracket in turn until it becomes clear which one has the lowest $I_{thresh}$. If it becomes more advantageous to determine the highest $I_{thresh}$ first, the algorithm may continue in the bracketing state until the bracket is found for every channel and then bisect each channel in descending order.

Figure 40:
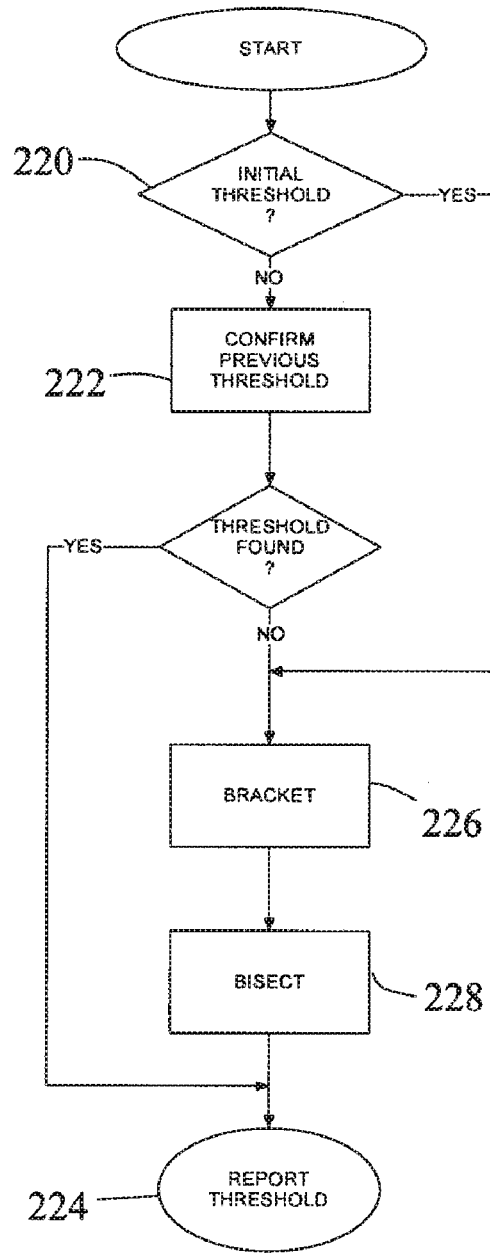
FIG. 40 is a flowchart illustrating the sequence employed by the algorithm to determine and monitor $I_{thresh}$.

FIG. 40 illustrates a further feature of the threshold hunting algorithm of the present invention, which advantageously provides the ability to further reduce the number of stimulations required to find $I_{thresh}$ when an $I_{thresh}$ value has previously been determined for a specific channel. In the event that a previous $I_{thresh}$ determination exists for a specific channel, the algorithm may begin by merely confirming the previous $I_{thresh}$ rather than beginning anew with the bracketing and bisection methods. The algorithm first determines whether it is conducting the initial threshold determination for the channel or whether there is a previous $I_{thresh}$ determination (step 220). If it is not the initial determination, the algorithm confirms the previous determination (step 222) as described below. If the previous threshold is confirmed, the algorithm reports that value as the present $I_{thresh}$ (step 224). If it is the initial $I_{thresh}$ determination, or if the previous threshold cannot be confirmed, then the algorithm performs the bracketing function (step 226) and bisection function (step 228) to determine $I_{thresh}$ and then reports the value (step 224).

Figure 41:
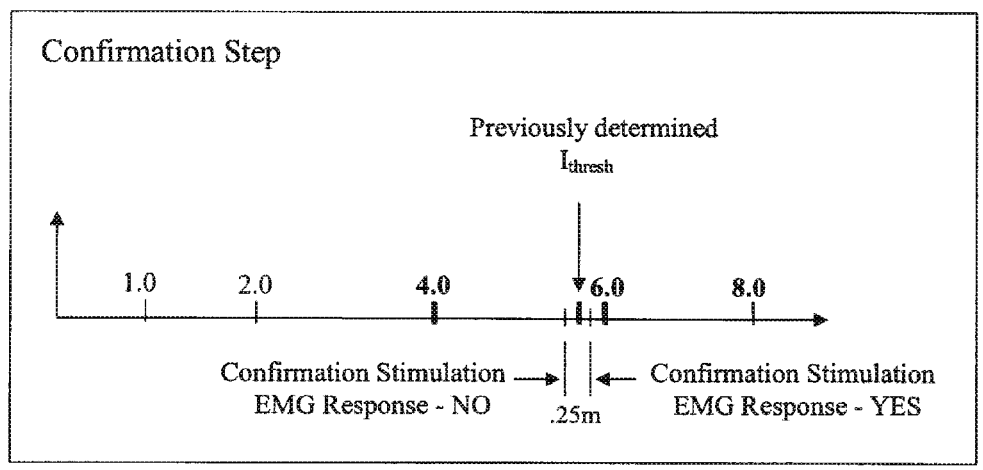
FIG. 41 is a graph illustrating the confirmation step employed by the algorithm to determine whether $I_{thesh}$ has changed from a previous determination.

FIG. 41 illustrates, by way of example only, a method employed by the threshold hunting algorithm for confirming a previous threshold. The confirmation step attempts to ascertain whether $I_{thresh}$ has moved from its last known value. To do this, the algorithm applies two stimulation currents, one at or just above the threshold value and the other just below the threshold value. If the stimulation at or above $I_{thresh}$ recruits and the stimulation just below $I_{thresh}$ does not recruit, then the threshold has not moved and the algorithm may report that value as $I_{thresh}$ and proceed to process another channel. If the stimulation just below $I_{thresh}$ recruits, it may be concluded that $I_{thresh}$ has decreased and likewise if the stimulation at or just above $I_{thresh}$ fails to recruit, it may be concluded that $I_{thresh}$ has increased.

If $I_{thresh}$ cannot be confirmed, the algorithm enters the bracketing state. Rather than beginning the bracketing state from the minimum stimulation current, however, the bracketing state may begin from the previous $I_{thresh}$. The bracketing may advance up or down depending on whether $I_{thresh}$ has increased or decreased. By way of example only, if the previous value of $I_{thresh}$ was 4 mA, the confirmation step may stimulate at 4 mA and 3.75 mA. If the stimulation at 4 mA fails to evoke a significant response, it may be concluded that the $I_{thresh}$ has increased and the algorithm will bracket up from 4 mA. When the algorithm enters the bracketing state, the increment used in the confirmation step (i.e. 0.25 mA in this example) is doubled. Thus, in this example, the algorithm stimulates at 4.50 mA. If the channel fails to recruit at this current level, the increment is doubled again (1 mA in this example) and the algorithm stimulates at 5.50 mA. This process is repeated until the maximum stimulation current is reached or the channel recruits, at which time the bisection function may be performed. If, during the confirmation step, the stimulation current just below the previously determined $I_{thresh}$ recruits, it may be concluded that $I_{thresh}$ for that channel has decreased and the algorithm may bracket down from that value (3.75 mA in this case). Thus, in this example, the algorithm would double the increment to 0.50 mA and stimulate at 3.25 mA. If the channel still recruits at this stimulation current, the increment is doubled again to 1 mA such that the algorithm stimulates at 2.25 mA. This process is repeated until the minimum stimulation current is reached or the channel fails to recruit, at which time the algorithm may perform the bisection function. When determining $I_{thresh}$ for multiple channels with previously determined $I_{thresh}$ values, this technique may be performed for each channel, in turn, in any order. Again stimulations may be omitted and the algorithm may begin processing a new channel before completing the algorithm for another channel, as described above.

While this invention has been described in terms of a best mode for achieving this invention's objectives, it will be appreciated by those skilled in the art that variations may be accomplished in view of these teachings without deviating from the spirit or scope of the present invention. By way of example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. As can be envisioned by one of skill in the art, many different combinations of the above may be used and accordingly the present invention is not limited by the specified scope.

What is claimed is:

1. A method of filtering electromyography signals to reject noise artifacts while performing free-run EMG monitoring, comprising the steps of:
   a) detecting an EMG signal with a sensor in electrical communication with a control unit;
   b) determining the signal-to-noise ratio of the amplitude of the voltage of the EMG signal with the control unit;
   c) classifying the signal as noise if the signal-to-noise ratio is lower than a predetermined value with the control unit; and
   d) assessing the amplitude of the voltage of the EMG signal and signaling an alert with the control unit if the EMG signal is greater or equal to a predetermined amplitude value.

2. The method of claim 1, wherein the signal-to-noise ratio is calculated by dividing the EMG signal voltage amplitude squared by the noise RMS value squared and converting to decibels.

3. The method of claim 1, wherein the predetermined value of the signal-to-noise ratio is 6.0 decibels.

4. The method of claim 1, wherein the amplitude of the voltage of the EMG signal is measured as a peak-to-peak voltage.

5. The method of claim 1, comprising the additional step of bypassing the alert if the signal is classified as noise based on the signal-to-noise ratio.

6. The method of claim 1, wherein the noise artifact forms a sine wave.

7. The method of claim 6, wherein the sine wave has a frequency of 60 Hz.

8. The method of claim 1, wherein the noise artifact forms a triangular wave.

\* \* \* \* \*